(12) United States Patent
Rodriguez et al.

(10) Patent No.: US 12,186,098 B2
(45) Date of Patent: Jan. 7, 2025

(54) SYSTEMS FOR MEDICAL DEVICE BREATHABILITY

(71) Applicant: MEDTRONIC MINIMED, INC., Northridge, CA (US)

(72) Inventors: Jasson Rodriguez, Rosemead, CA (US); Ellis Garai, Studio City, CA (US); Ravi R. Deverkadra, Simi Valley, CA (US); Sara M. Voisin, Chatsworth, CA (US); Jacob E. Pananen, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 480 days.

(21) Appl. No.: 16/785,462

(22) Filed: Feb. 7, 2020

(65) Prior Publication Data
US 2021/0244357 A1  Aug. 12, 2021

(51) Int. Cl.
*A61B 5/145* (2006.01)
*A61B 5/00* (2006.01)

(52) U.S. Cl.
CPC ........ *A61B 5/6833* (2013.01); *A61B 5/14532* (2013.01); *A61B 2560/04* (2013.01); *A61B 2562/02* (2013.01)

(58) Field of Classification Search
CPC ............. A61B 5/6833; A61B 5/14532; A61B 2560/04; A61B 2562/02
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |

(Continued)

FOREIGN PATENT DOCUMENTS

WO  2019222615 A1  11/2019
WO  2019239258 A1  12/2019

*Primary Examiner* — Puya Agahi
*Assistant Examiner* — Grace L Rozanski
(74) *Attorney, Agent, or Firm* — Foley & Lardner LLP

(57) ABSTRACT

A medical device includes a sensor to observe a characteristic of an anatomy, and a sensor base coupled to the sensor. The medical device includes a coupling system to couple the sensor base to the anatomy. The coupling system includes a first adhesive member and a second adhesive member. The first adhesive member is coupled to the sensor base and the second adhesive member is to couple to the anatomy. The second adhesive member includes at least one cut-out to direct moisture to an ambient environment surrounding the medical device.

11 Claims, 12 Drawing Sheets

(56) References Cited

U.S. PATENT DOCUMENTS

| | | |
|---|---|---|
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | McIvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,295,786 B2 | 3/2016 | Gottlieb et al. |
| 2007/0123819 A1 | 5/2007 | Mernoe et al. |
| 2008/0249383 A1 | 10/2008 | Sass et al. |
| 2009/0299301 A1 | 12/2009 | Gottlieb et al. |
| 2010/0160861 A1 | 6/2010 | Causey, III et al. |
| 2013/0267813 A1 | 10/2013 | Pryor et al. |
| 2014/0378799 A1* | 12/2014 | Chattaraj .................. B32B 7/12 600/300 |
| 2016/0058380 A1* | 3/2016 | Lee ....................... A61B 5/6832 600/365 |
| 2016/0310051 A1 | 10/2016 | Brister et al. |
| 2017/0290533 A1 | 10/2017 | Antonio et al. |
| 2017/0367895 A1* | 12/2017 | Holm ..................... B32B 5/024 |
| 2019/0083037 A1 | 3/2019 | Bremer |
| 2019/0167167 A1 | 6/2019 | Mitchell et al. |
| 2020/0085349 A1* | 3/2020 | Bremer .............. A61B 5/14532 |
| 2020/0163844 A1 | 5/2020 | Pang et al. |
| 2021/0161437 A1 | 6/2021 | Thomas et al. |
| 2021/0204841 A1 | 7/2021 | Thomas et al. |
| 2021/0236028 A1* | 8/2021 | Mccanless ........ A61B 5/14503 |
| 2021/0244357 A1 | 8/2021 | Rodriguez et al. |

\* cited by examiner

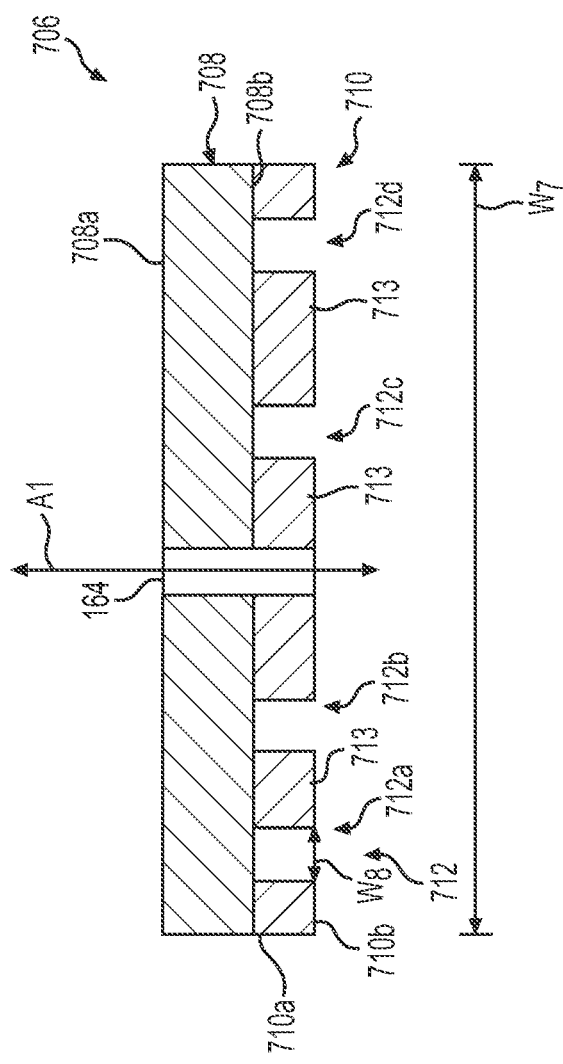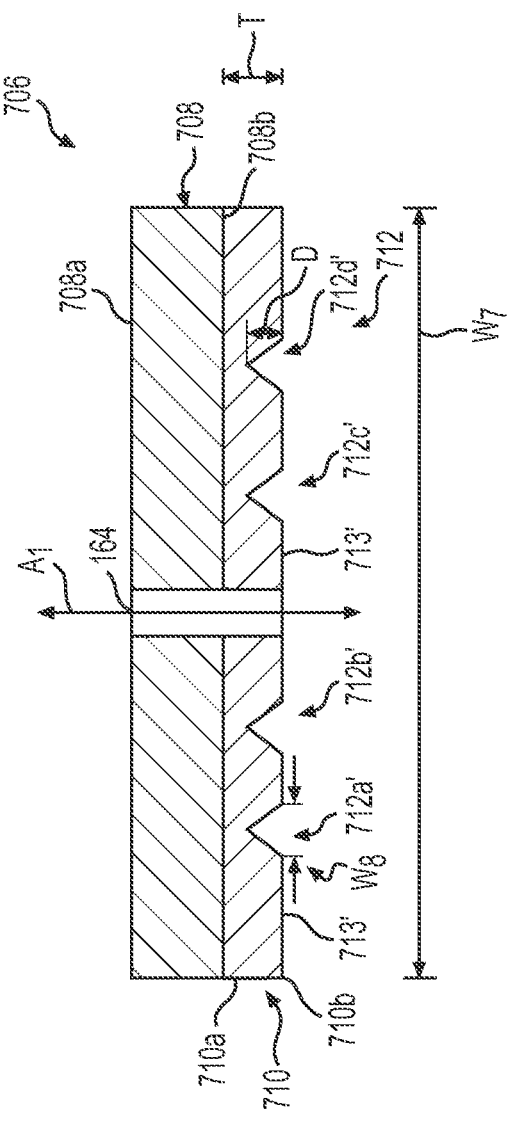

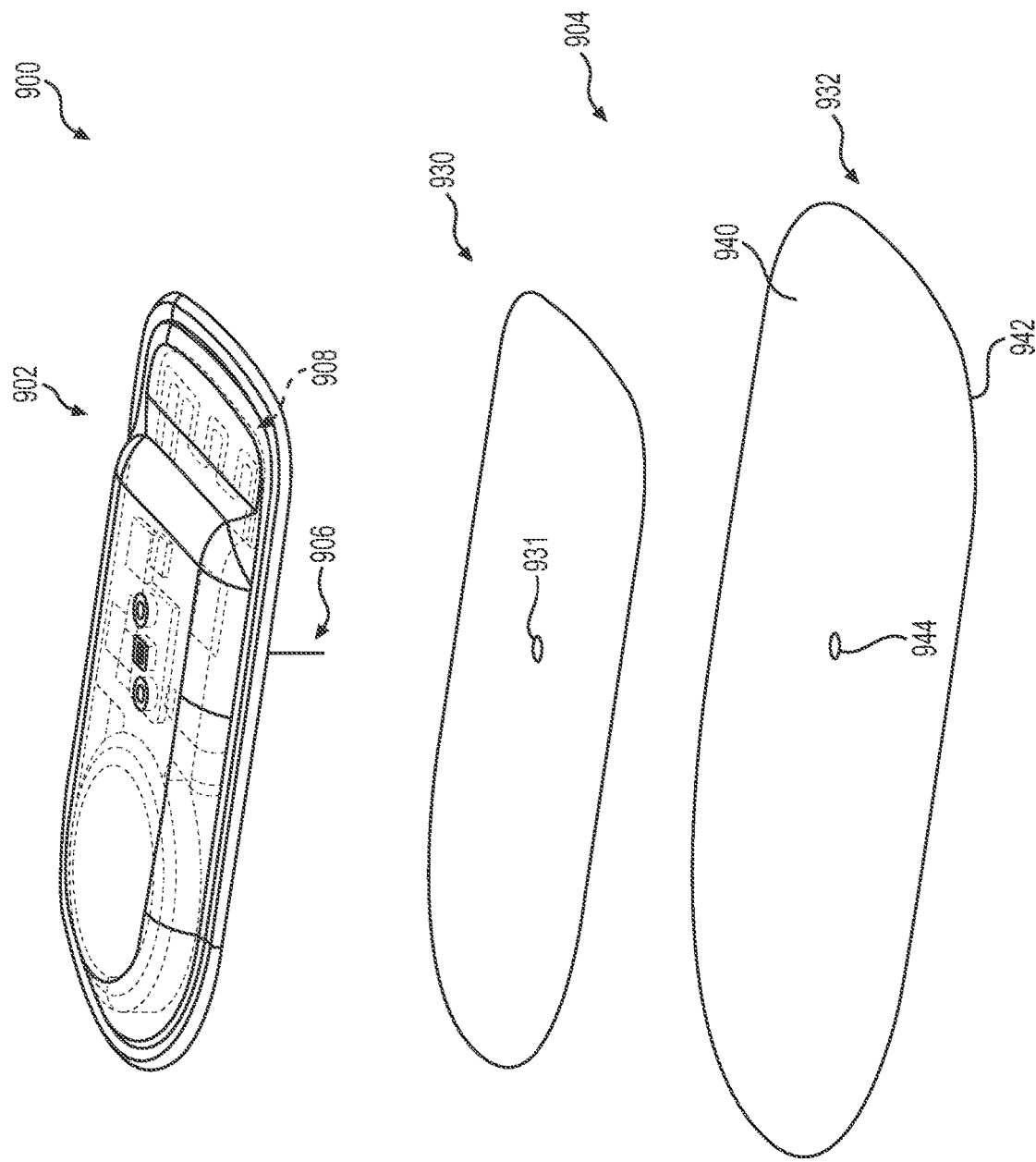

SYSTEMS FOR MEDICAL DEVICE BREATHABILITY

FIELD

Embodiments of the subject matter described herein relate generally to medical devices, such as a physiological characteristic sensor assembly and a skin adhesive patch. More particularly, embodiments of the subject matter relate to systems that improve breathability of the physiological characteristic sensor assembly and the skin adhesive patch to improve user comfort.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product, such as a continuous glucose monitor, which is adhered to the patient during use via an adhesive skin patch. As the patient wears the continuous glucose monitor, which is coupled to the user via the adhesive skin patch, the patient may be exposed to moisture, such as during rain, swimming, bathing, etc. The exposure to moisture, over time, may cause the moisture to accumulate between the continuous glucose monitor and/or adhesive skin patch, which may cause discomfort to the user. Further, the exposure to moisture may cause the adhesive skin patch to become uncoupled from the user or may cause irritation to the skin of the user.

Accordingly, it is desirable to provide systems for improving breathability of a medical device, such as an adhesive skin patch and a physiological characteristic sensor assembly, for example, a glucose sensor or continuous glucose monitor, which enables moisture to transfer into the surrounding environment or to be directed away from the medical device. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to systems that improve breathability of a medical device, such as a glucose sensor or continuous glucose monitor, by transferring or directing moisture from the medical device into the surrounding environment.

According to various embodiments, provided is a medical device. The medical device includes a sensor to observe a characteristic of an anatomy, and a sensor base coupled to the sensor. The medical device includes a coupling system to couple the sensor base to the anatomy. The coupling system includes a first adhesive member and a second adhesive member. The first adhesive member is coupled to the sensor base and the second adhesive member is to couple to the anatomy. The second adhesive member includes at least one cut-out to direct moisture to an ambient environment surrounding the medical device.

Further provided is a medical device. The medical device includes a sensor to observe a characteristic of an anatomy, and a sensor base coupled to the sensor. The medical device includes a coupling system to couple the sensor base to the anatomy. The coupling system includes a first adhesive member and a second adhesive member. The first adhesive member is coupled to the sensor base and the second adhesive member is to couple to the anatomy. The second adhesive member includes a backing layer coupled to the first adhesive member and a skin adhesive layer to couple to the anatomy. The second adhesive member includes at least one cut-out defined through at least one of the backing layer and the skin adhesive layer to direct moisture to an ambient environment surrounding the medical device.

Also provided according to various embodiments is a medical device. The medical device includes a sensor to observe a characteristic of an anatomy, and a sensor base coupled to the sensor. The medical device includes a coupling system to couple the sensor base to the anatomy. The coupling system includes a first adhesive member and a second adhesive member. The first adhesive member is coupled to the sensor base and the second adhesive member is to couple to the anatomy. The first adhesive member includes at least one cut-out to direct moisture to an ambient environment surrounding the medical device.

Further provided is a medical device. The medical device includes a sensor to observe a characteristic of an anatomy, and a sensor base coupled to the sensor. The medical device includes a coupling system to couple the sensor base to the anatomy. The coupling system includes a first adhesive member and a second adhesive member. The first adhesive member is coupled to the sensor base and the second adhesive member is to couple to the anatomy. The first adhesive member includes a central bore to receive the sensor and a plurality of cut-outs spaced apart about the central bore to direct moisture to an ambient environment surrounding the medical device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 11 is a cross-sectional view of the second adhesive member of FIG. 10, taken along line 11-11 of FIG. 10;

FIG. 12 is a cross-sectional view of another embodiment for the second adhesive member of FIG. 10, taken from the perspective of line 11-11 of FIG. 10;

FIG. 15 is a partially exploded view of another exemplary medical device having increased breathability according to various teachings of the present disclosure.

DETAILED DESCRIPTION

Figure 1:
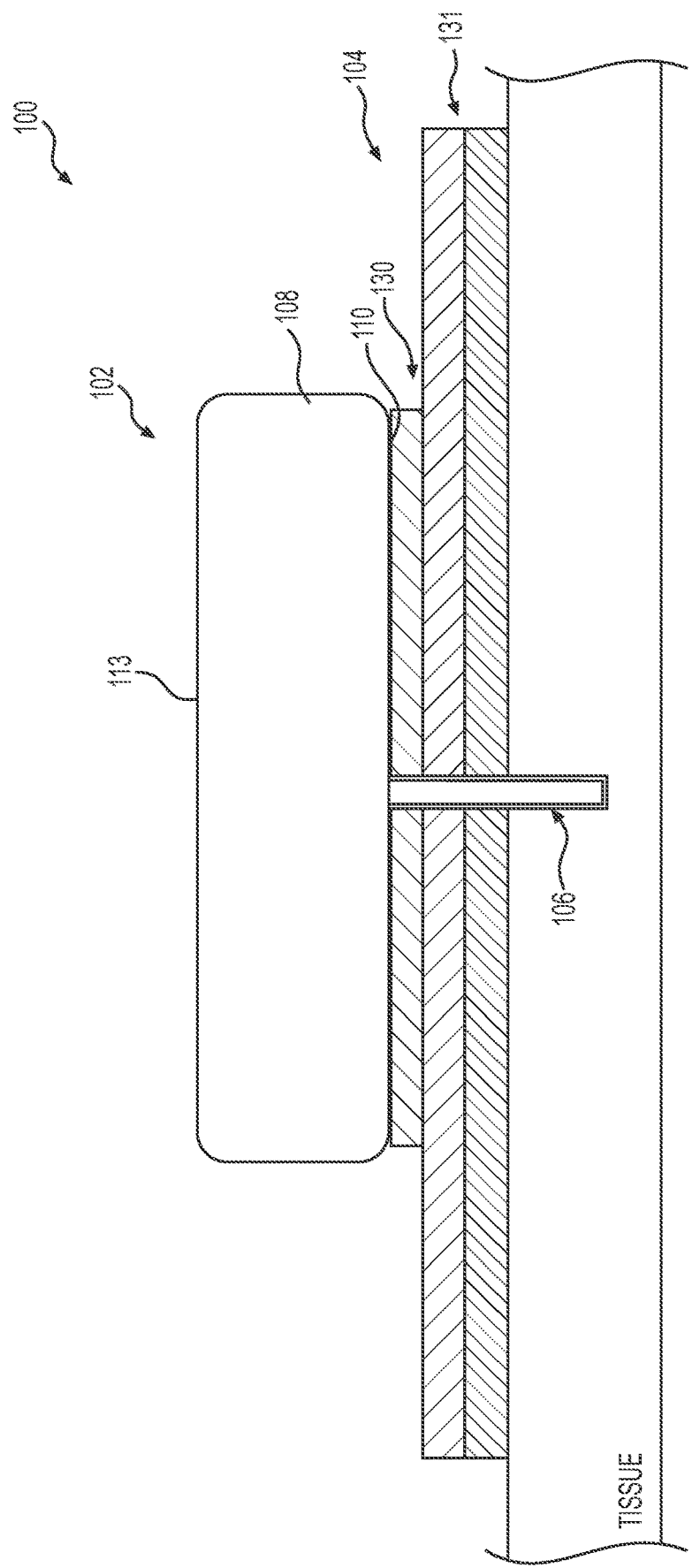
FIG. 1 is a side view of an exemplary medical device having increased breathability according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of systems for breathability for a medical device, such as a medical device that is coupled to a user with an adhesive skin patch. The systems described herein enable liquids, such as water, to be directed away from the medical device and/or adhesive skin patch, which enables the medical device and/or adhesive skin patch to remain coupled to the user for longer periods of time, while also improving comfort. It should be noted that while the adhesive skin patch is described herein as being used with a medical device, such as a glucose sensor, for example, a glucose sensor associated with a continuous glucose monitor, it will be understood that the adhesive skin patch may be employed with a variety of other sensors, such as cardiac monitors, body temperature sensors, EKG monitors etc., other medical devices, and/or other components that are intended to be affixed to the body of a user. Moreover, the medical device is not limited to a continuous glucose monitor, but may encompass cardiac monitors, body temperature sensors, EKG monitors etc., and/or other components that are intended to be affixed to the body of a user. Thus, while the non-limiting examples described below relate to improving breathability of a medical device used to treat diabetes (more specifically, an adhesive skin patch coupled to a continuous glucose monitor), embodiments of the disclosed subject matter are not so limited.

Generally, the glucose sensor employed with the medical device is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein).

With reference to FIG. 1, FIG. 1 is a perspective view of a medical device 100. In one example, the medical device 100 is a wearable medical device, which in this example includes a physiological characteristic sensor assembly 102 and a coupling system 104. It should be noted that in certain embodiments, the physiological characteristic sensor assembly 102 may comprise the sensor transmitter assembly described in commonly assigned U.S. Patent Publication No. 2017/0290533 to Antonio, et al., the relevant portion of which is incorporated herein by reference. Generally, the physiological characteristic sensor assembly 102 and the coupling system 104 are coupled together as a single unit. The physiological characteristic sensor assembly 102 and the coupling system 104 may be packaged together for use by a consumer.

Certain features, aspects, and characteristics of the physiological characteristic sensor assembly 102 may be conventional and, as such, will not be described in detail here. Briefly, the physiological characteristic sensor assembly 102 can be pre-connected as part of a sensor set, which could also include a sensor electronics module (not shown), such as a wireless transmitter that communicates with an infusion pump, a monitor device, or the like, which connects to the physiological characteristic sensor assembly 102 after the insertion or deployment of a portion of the physiological characteristic sensor assembly 102 in the body of the user. In one example, the physiological characteristic sensor assembly 102 includes a glucose sensor 106 and a sensor base 108. It should be noted that the physiological characteristic sensor assembly 102 is not limited to a continuous glucose monitor, but rather, various other physiological characteristic sensors may be employed. The glucose sensor 106 may be provided as an integral part of the sensor base 108. The sensor base 108 gives structural support to the glucose sensor 106, and facilitates entry of the glucose sensor 106 into the body of the user. The glucose sensor 106 is an electrochemical sensor that includes the glucose oxidase enzyme, as is well understood by those familiar with glucose sensor technology. The glucose oxidase enzyme enables the glucose sensor 106 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, the glucose sensor 106 is positionable in subcutaneous tissue of the user by an insertion needle of a sensor inserter to measure the glucose oxidase enzyme.

The sensor base 108 is coupled to the coupling system 104. The sensor base 108 may also feature electrical and physical interfaces and elements that accommodate the sensor electronics module, such as the wireless transmitter that communicates with the infusion pump, the monitor device, or the like. In certain embodiments the sensor base 108 is composed at least in part from a plastic material. For the embodiment described here, the bulk of the sensor base 108 is formed as a molded plastic component. In one example, the sensor base 108 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

Figure 2:
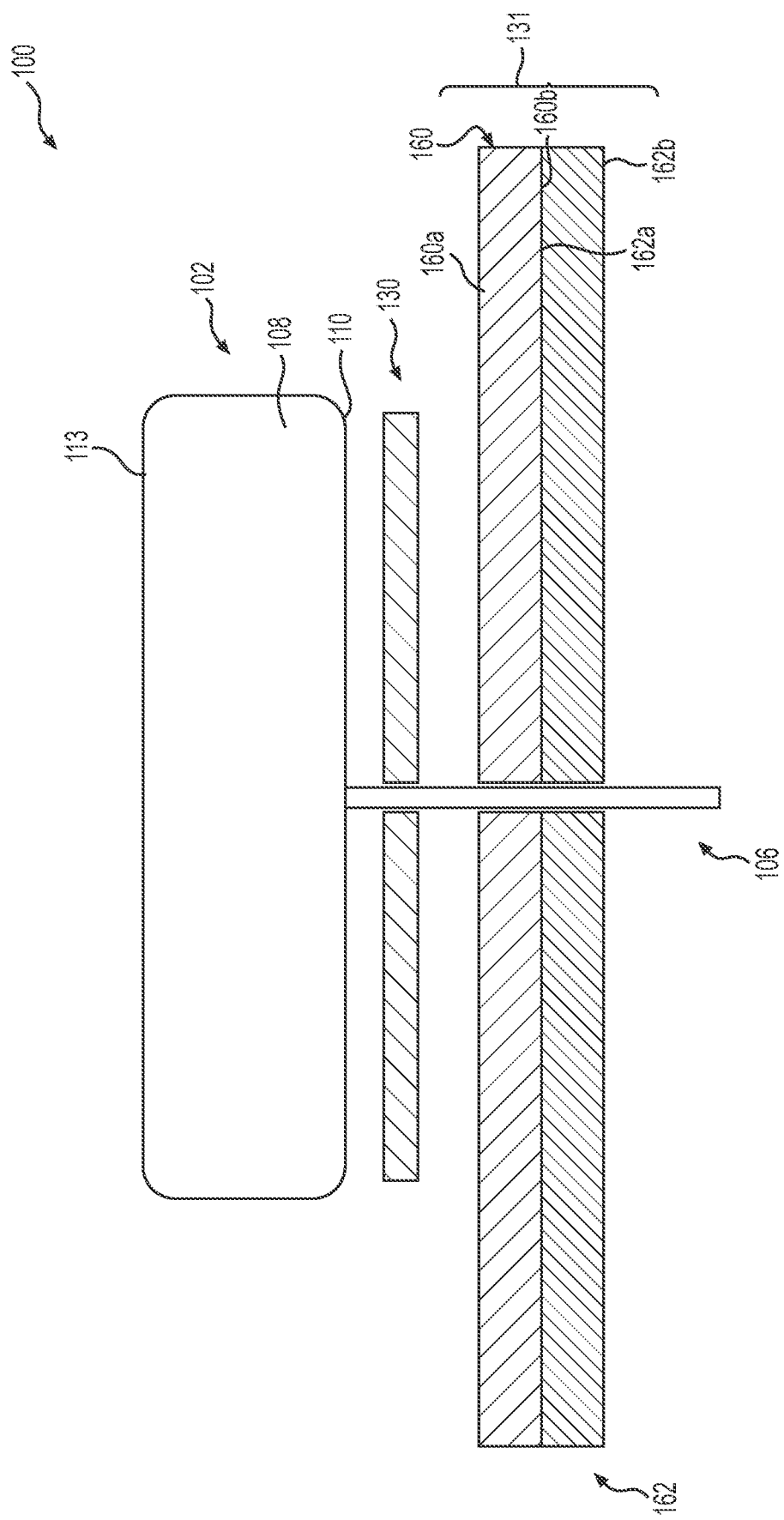
FIG. 2 is a partially exploded side view of the medical device of FIG. 1.
Figure 3:
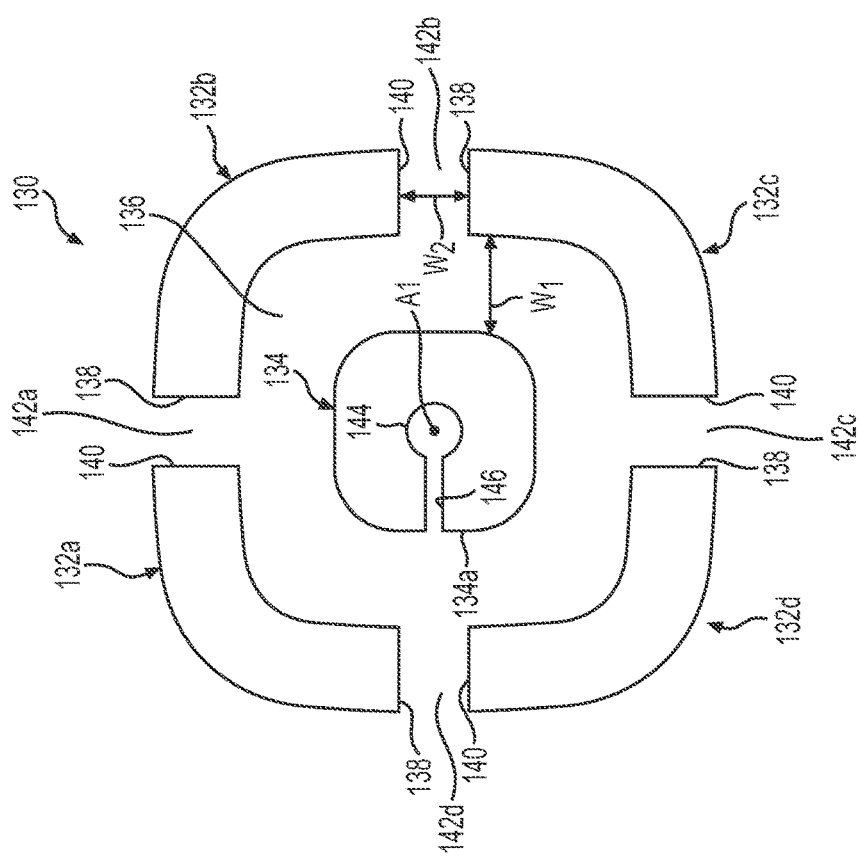
FIG. 3 is a top view of an exemplary first adhesive member that provides increased breathability for use with the medical device of FIG. 1.

In one example, with reference to FIG. 2, an exploded view of the medical device 100 is shown. As shown, the coupling system 104 includes a first adhesive member 130 and a second adhesive member 131. The first adhesive member 130 couples the sensor base 108 to the second adhesive member 131. In this example, the first adhesive member 130 is a double-sided pressure sensitive adhesive. In one example, the first adhesive member 130 is composed of a synthetic rubber, acrylic-based adhesive or a non-woven polyester tape. In one example, the first adhesive member 130 is a moisture guidance system. Thus, in this example, the first adhesive member 130 is defined to direct moisture, fluids, etc. away from the physiological characteristic sensor assembly 102. With reference to FIG. 3, the first adhesive member 130 is shown in greater detail.

In one example, the first adhesive member 130 includes a plurality of adhesive sections 132 and a central hub section 134, which cooperate to couple the sensor base 108 to the second adhesive member 131. In this example, the first adhesive member 130 includes four sections 132a-132d, however, the first adhesive member 130 may include any number of sections 132. The four sections 132a-132d are symmetrical about an axis A1; however, the sections 132a-132d may be asymmetrical if desired. The sections 132a-132d are spaced apart from the central hub section 134 to define a main channel 136, which surrounds the central hub section 134. The sections 132a-132d cooperate to define a shape that corresponds to a shape of the sensor base 108, which in this example, is substantially rectangular. In this example, each of the sections 132a-132d is elbow shaped, however, the sections 132a-132d may have any desired shape. Each of the sections 132a-132d has a first section end 138 opposite a second section end 140. The ends 138, 140 of adjacent sections 132a-132d are spaced apart to define intermediate channels 142a-142d. The intermediate channels 142a-142d are in communication with the main channel 136 to direct moisture, fluids, etc. from proximate the central hub section 134 to the terminal end 110b (FIG. 1) of the physiological characteristic sensor assembly 102. The intermediate channels 142a-142d are defined proximate a perimeter of the sensor base 108 when the sensor base 108 is coupled to the first member 130.

The main channel 136 surrounds the central hub section 134, and directs moisture, fluids, etc. from proximate the central hub section 134 to the intermediate channels 142a-142d, from which the moisture, fluids, etc. may flow to the terminal end 110b (FIG. 1). Generally, the main channel 136 and the intermediate channels 142a-142d are defined as cut-outs in the first adhesive member 130. The main channel 136 may have a width W1 of 0.05 inches (in.) to about 0.4 inches (in.), and each intermediate channel 142a-142d may have a width W2 of about 0.05 inches (in.) to about 0.4 inches (in.). Generally, the main channel 136 and the intermediate channels 142a-142d reduce a bonding surface area of the first adhesive member 130 by about 50%. The reduced bonding surface area created by the main channel 136 and the intermediate channels 142a-142d also improves conformity by providing greater flexibility between the second adhesive member 131 and the sensor base 108.

The central hub section 134 is defined at a center of the first adhesive member 130. The central hub section 134 is substantially rectangular, however, the central hub section 134 may have any desired shape. The central hub section 134 defines a central bore 144 and a slit 146. The central bore 144 is sized to enable the glucose sensor 106 (FIG. 2) to pass through the first adhesive member 130. The central bore 144 is coaxial with the axis A1. The slit 146 is in communication with the central bore 144 to enable the first adhesive member 130 to be positioned about the glucose sensor 106 (FIG. 2). Generally, the slit 146 extends from a first side 134a of the central hub section 134 to the central bore 144.

Thus, the first adhesive member 130 is defined with cut-outs or the main channel 136 and the intermediate channels 142a-142d to direct moisture, fluids, etc. from near the center of the physiological characteristic sensor assembly 102 (FIG. 1) toward the terminal end 110b. The intermediate channels 142a-142d cooperate with the main channel 136 to direct the moisture away from the physiological characteristic sensor assembly 102, which improves a breathability of the physiological characteristic sensor assembly 102 by increasing the moisture vapor transmission rate while also improving user comfort.

Figure 4:
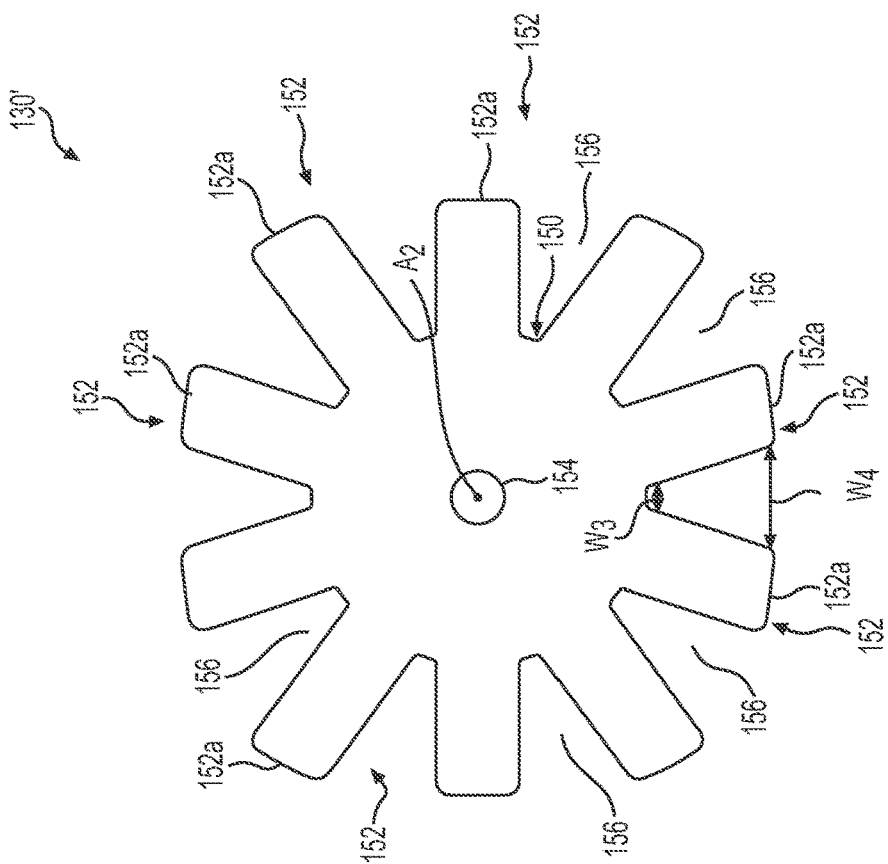
FIG. 4 is a top view of another exemplary first adhesive member that provides increased breathability for use with the medical device of FIG. 1.

It should be noted that in other embodiments, the first adhesive member 130 may be configured differently to improve breathability by increasing the moisture vapor transmission rate and directing moisture, fluids, etc. from the physiological characteristic sensor assembly 102 while coupling the sensor base 108 to the second adhesive member 131. For example, with reference to FIG. 4, a first adhesive member 130' is shown. As the first adhesive member 130' includes the same or similar components as the first adhesive member 130 discussed with regard to FIGS. 1-3, the same reference numerals will be used to denote the same or similar components. In this example, the first adhesive member 130' is a double-sided pressure sensitive adhesive, and is composed of a synthetic rubber, acrylic-based adhesive or a non-woven polyester tape. In this example, the first adhesive member 130' includes a central hub section 150 and a plurality of spokes 152. The first adhesive member 130' is symmetric with respect to an axis A2. The central hub section 150 is substantially circular, and is sized to be coupled to the sensor base 108 (FIG. 1). The central hub section 150 defines a central bore 154, which is sized to enable the glucose sensor 106 (FIG. 2) to pass through the first adhesive member 130'. The central bore 154 is coaxial with the axis A2.

The plurality of spokes 152 extend radially outward from the central hub section 150. The spokes 152 provide an additional bonding surface for coupling the sensor base 108 to the second adhesive member 131. Each of the spokes 152 is substantially rectangular, however, the spokes 152 may have any desired shape. The spokes 152 extend radially outward from the central hub section 150 to define a plurality of channels 156. Each of the channels 156 are substantially triangular in shape, and are defined between adjacent spokes 152. Thus, the channels 156 may have a width W3 at the central hub section 150 that is different, and less than, a width W4 at terminal ends 152a of the spokes 152. In one example, the width W3 is about 0.005 inches (in.) to about 0.020 inches (in.); and the width W4 is about 0.05 inches (in.) to about 0.4 inches (in.). The channels 156 are defined as cut-outs in the first adhesive member 130' that are spaced apart about a perimeter of the first adhesive member 130'. The channels 156 direct moisture, fluids, etc. from proximate the central hub section 150 to the terminal end 110b (FIG. 1) of the physiological characteristic sensor assembly 102.

Generally, the central hub section 150 and the spokes 152 reduce a bonding surface area of the first adhesive member 130' by about 50% when compared to a solid adhesive member. The reduced bonding surface area created by the central hub section 150 and the spokes 152 also improves conformity by providing greater flexibility between the second adhesive member 131 and the sensor base 108. The channels 156 defined between the spokes 152 direct moisture, fluids, etc. from near the center of the physiological characteristic sensor assembly 102 (FIG. 1) toward the terminal end 110b, which improves a breathability of the physiological characteristic sensor assembly 102 while also improving user comfort.

With reference back to FIG. 2, the second adhesive member 131 couples the physiological characteristic sensor assembly 102 to the user. In one example, the second adhesive member 131 includes a backing layer 160, a skin adhesive layer 162 and defines a central bore 164. The backing layer 160 and the skin adhesive layer 162 cooperate to define an adhesive skin patch for coupling the physiological characteristic sensor assembly 102 to the user. The backing layer 160 is composed of a nonwoven polyurethane, for example. The backing layer 160 has a first surface 160a coupled to the first adhesive member 130, and an opposite second surface 160b coupled to the skin adhesive layer 162. The skin adhesive layer 162 is composed of an acrylic adhesive, which may be painted, coated or otherwise formed on the backing layer 160. One side 162a of the skin adhesive layer 162 is coupled to the backing layer 160, and a second opposite side 162b is configured to be coupled to an anatomy, such as a skin of a user, when the physiological characteristic sensor assembly 102 is deployed on the user. The central bore 164 is coaxially aligned with the respective central bore 144, 154 of the respective first adhesive member 130, 130' to enable the glucose sensor 106 to pass through the second adhesive member 131. Thus, the central bore 164 is defined through both the backing layer 160 and the skin adhesive layer 162.

In one example, with reference to FIG. 1, with the physiological characteristic sensor assembly 102 assembled, the skin adhesive layer 162 is coupled to the backing layer 160 to form the second adhesive member 131. The first adhesive member 130 is coupled to the second adhesive member 131, and is coupled to the sensor base 108. Alternatively, the first adhesive member 130' may be coupled between the second adhesive member 131 and the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 is positioned within a tissue of the user and the skin adhesive layer 162 is coupled to the anatomy or skin of the user. With the medical device 100 coupled to the user, the user may perform their daily activities with increased comfort and breathability as the main channel 136 and the intermediate channels 142a-142d increase the moisture vapor transmission rate. In this regard, as discussed, the main channel 136 and the intermediate channels 142a-142d of the first adhesive member 130 cooperate to direct moisture, fluids, etc. away from the glucose sensor 106 toward the terminal end 110b of the sensor base 108, which improves breathability of the medical device 100. Similarly, the channels 156 defined between the spokes 152 increase the moisture vapor transmission rate and direct moisture, fluids, etc. away from the glucose sensor 106 toward the terminal end 110b of the sensor base 108, which improves breathability of the medical device 100. Moreover, the reduced bonding area of the first adhesive member 130, 130' between the physiological characteristic sensor assembly 102 and the second adhesive member 131 provides increased conformity of the medical device 100 to the anatomy of the user.

Figure 5:
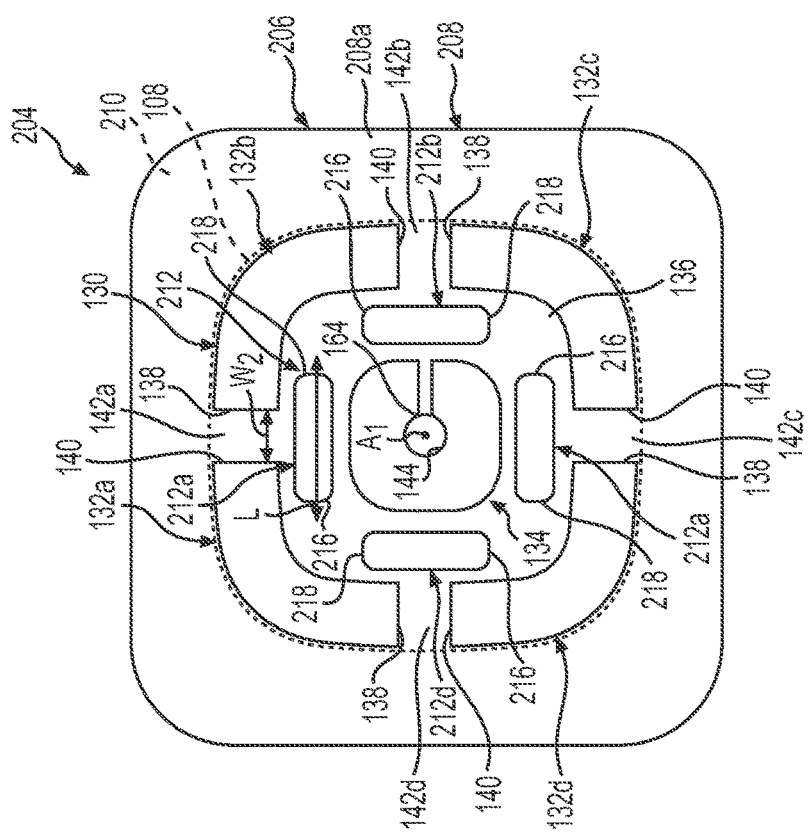
FIG. 5 is a top view of an exemplary coupling system that provides increased breathability for use with the medical device of FIG. 1.

It should be noted that in other embodiments, the coupling system 104 may be configured differently to improve breathability by increasing the moisture vapor transmission rate and directing moisture, fluids, etc. away from the medical device 100. For example, with reference to FIG. 5, a coupling system 204 is shown. As the coupling system 204 includes the same or similar components as the coupling system 104 discussed with regard to FIGS. 1-4, the same reference numerals will be used to denote the same or similar components. FIG. 5 is a schematic top view of the coupling system 204. In this example, the coupling system 204 includes the first adhesive member 130 and a second adhesive member 206. The first adhesive member 130 couples the sensor base 108 to the second adhesive member 206. As discussed, the first adhesive member 130 is a moisture guidance system, which in this example, cooperates with the second adhesive member 206 to further direct moisture, fluids, etc. away from the user and the physiological characteristic sensor assembly 102.

The second adhesive member 206 couples the physiological characteristic sensor assembly 102 (FIG. 1) to the user. A perimeter of the sensor base 108 of the physiological characteristic sensor assembly 102 is shown in FIG. 5 by a dashed line. In one example, the second adhesive member 206 includes a backing layer 208, a skin adhesive layer 210, the central bore 164 and at least one or a plurality of cut-outs 212. The backing layer 208 and the skin adhesive layer 210 cooperate to define an adhesive skin patch for coupling the physiological characteristic sensor assembly 102 (FIG. 1) to the user. The backing layer 208 is composed of a nonwoven polyurethane, for example. The backing layer 208 has a first surface 208a coupled to the first adhesive member 130, and an opposite second surface coupled to the skin adhesive layer 210. The skin adhesive layer 210 is composed of an acrylic adhesive, which may be painted, coated or otherwise formed on the backing layer 208. One side of the skin adhesive layer 210 is coupled to the backing layer 208, and a second opposite side is configured to be coupled to an anatomy, such as a skin of a user, when the physiological characteristic sensor assembly 102 is deployed on the user. The central bore 164 is coaxially aligned with the central bore 144 of the first adhesive member 130 to enable the glucose sensor 106 to pass through the second adhesive member 206. Thus, the central bore 164 is defined through both the backing layer 208 and the skin adhesive layer 210.

The cut-outs 212 are defined through both the backing layer 208 and the skin adhesive layer 210 such that the cut-outs 212 define areas of the second adhesive member 206 that are devoid of material or are open. The cut-outs 212 enable communication between the anatomy or skin of the user and the coupling system 204, which enables moisture, such as sweat, on the skin of the user to be directed into the ambient environment and away from the physiological characteristic sensor assembly 102. In one example, the second adhesive member 206 defines four cut-outs 212a-212d, however, the second adhesive member 206 may define any number of cut-outs 212. The cut-outs 212a-212d are spaced apart about the first surface 208a of the backing layer 208, and thus, about a perimeter of the second adhesive member 206. In this example, each of the cut-outs 212a-212d is oblong, discorectangle or stadium in shape; however, the cut-outs 212a-212d may have any desired shape.

Each of the cut-outs 212a-212d has a first end 216 opposite a second end 218, and extend along a longitudinal axis L from the first end 216 to the second end 218. The longitudinal axis L is transverse to, and in this example, substantially perpendicular to, the axis A1. In this example, the cut-outs 212a-212d are arranged to be aligned with the central hub section 134, and are in communication with the main channel 136 of the first adhesive member 130 to promote the transfer of moisture, fluid, etc. from the anatomy of the user to the main channel 136 and from the main channel 136 to the intermediate channels 142a-142d when the first adhesive member 130 is coupled to the second adhesive member 206. The cut-outs 212a-212d are defined such that each of the first end 216 and the second end 218 extend beyond or across the respective intermediate channel 142a-142d of the first adhesive member 130. Stated another way, each of the cut-outs 212a-212d has a length along the longitudinal axis L, which is greater than the width W2 of the respective intermediate channel 142a-142d. By extending beyond the respective intermediate channel 142a-142d, the cut-outs 212a-212d have a greater surface area to channel moisture, fluids, etc. from the user to the main channel 136 and to the respective intermediate channel 142a-142d. The cut-outs 212a-212d are defined through the second adhesive member 206 to be positioned within a perimeter of the sensor base 108.

The coupling system 204 may be used with the physiological characteristic sensor assembly 102 to couple the physiological characteristic sensor assembly 102 to the anatomy of the user, as discussed with regard to the coupling system 104. Briefly, with the physiological characteristic sensor assembly 102 (FIG. 1) assembled, the skin adhesive layer 210 is coupled to the backing layer 208 to form the second adhesive member 206. The cut-outs 212a-212d are defined through the backing layer 208 and the skin adhesive layer 210 via laser cutting, die cutting, etc. The first adhesive member 130 is coupled to the second adhesive member 206, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 210 is coupled to the anatomy or skin of the user. With the medical device 100 coupled to the user, the user may perform their daily activities with increased comfort and breathability as the cut-outs 212a-212d increase the moisture vapor transmission rate. In this regard, the cut-outs 212a-212d enable the moisture, fluids, etc. on the anatomy or skin of a user to escape to the ambient environment, and the main channel 136 and the intermediate channels 142a-142d of the first adhesive member 130 cooperate to direct the moisture, fluids, etc. toward the terminal end 110b of the sensor base 108, which improves breathability of the medical device 100. Moreover, the cut-outs 212a-212d of the second adhesive member 206 provides increased conformity and flexibility of the medical device 100 when coupled to the anatomy of the user by reducing the bonding area of the second adhesive member 206.

Figure 6:
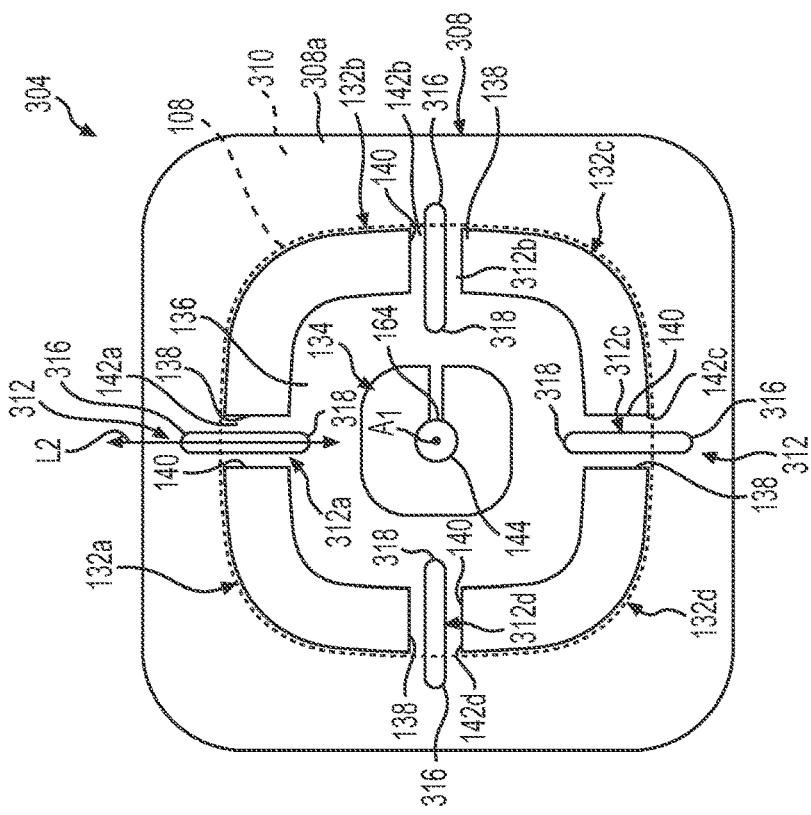
FIG. 6 is a top view of another exemplary coupling system that provides increased breathability for use with the medical device of FIG. 1.

It should be noted that in other embodiments, the coupling system 104 may be configured differently to improve breathability by increasing the moisture vapor transmission rate and directing moisture, fluids, etc. away from the medical device 100. For example, with reference to FIG. 6, a coupling system 304 is shown. As the coupling system 304 includes the same or similar components as the coupling system 104 discussed with regard to FIGS. 1-4, the same reference numerals will be used to denote the same or similar components. FIG. 6 is a schematic top view of the coupling system 304. In this example, the coupling system 304 includes the first adhesive member 130 and a second adhesive member 306. The first adhesive member 130 couples the sensor base 108 to the second adhesive member 306. As discussed, the first adhesive member 130 is a moisture guidance system, which in this example, cooperates with the second adhesive member 306 to further direct moisture, fluids, etc. away from the user and the physiological characteristic sensor assembly 102.

The second adhesive member 306 couples the physiological characteristic sensor assembly 102 (FIG. 1) to the user. A perimeter of the sensor base 108 of the physiological characteristic sensor assembly 102 is shown in FIG. 6 by a dashed line. In one example, the second adhesive member 306 includes a backing layer 308, a skin adhesive layer 310, the central bore 164 and at least one or a plurality of cut-outs 312. The backing layer 308 and the skin adhesive layer 310 cooperate to define an adhesive skin patch for coupling the physiological characteristic sensor assembly 102 (FIG. 1) to the user. The backing layer 308 is composed of a nonwoven polyurethane, for example. The backing layer 308 has a first surface 308a coupled to the first adhesive member 130, and an opposite second surface coupled to the skin adhesive layer 310. The skin adhesive layer 310 is composed of an acrylic adhesive, which may be painted, coated or otherwise formed on the backing layer 308. One side of the skin adhesive layer 310 is coupled to the backing layer 308, and a second opposite side is configured to be coupled to an anatomy, such as a skin of a user, when the physiological characteristic sensor assembly 102 is deployed on the user. The central bore 164 is coaxially aligned with the central bore 144 of the first adhesive member 130 to enable the glucose sensor 106 to pass through the second adhesive member 306. Thus, the central bore 164 is defined through both the backing layer 308 and the skin adhesive layer 310.

The cut-outs 312 are defined through both the backing layer 308 and the skin adhesive layer 310 such that the cut-outs 312 define areas of the second adhesive member 306 that are devoid of material or are open. The cut-outs 312 enable communication between the anatomy or skin of the user and the coupling system 304, which enables moisture, such as sweat, on the skin of the user to be directed into the ambient environment and away from the physiological characteristic sensor assembly 102. In one example, the second adhesive member 306 defines four cut-outs 312a-312d, however, the second adhesive member 306 may define any number of cut-outs 312. The cut-outs 312a-312d are spaced apart about the first surface 308a of the backing layer 308, and thus, about a perimeter of the second adhesive member 306. In this example, each of the cut-outs 312a-312d is oblong, discorectangle or stadium in shape; however, the cut-outs 312a-312d may have any desired shape.

Each of the cut-outs 312a-312d has a first end 316 opposite a second end 318, and extend along a longitudinal axis L1 from the first end 316 to the second end 318. The longitudinal axis L1 is transverse to, and in this example, substantially perpendicular to, the axis A1. In this example, the cut-outs 312a-312d are arranged to be aligned with the intermediate channels 142a-142d and are in communication with the intermediate channels 142a-142d of the first adhesive member 130 to promote the transfer of moisture, fluid, etc. from the anatomy of the user to the intermediate channels 142a-142d when the first adhesive member 130 is coupled to the second adhesive member 306. The cut-outs 312a-312d are defined such that each of the first end 316 and the second end 318 extend beyond the respective intermediate channel 142a-142d of the first adhesive member 130. By extending beyond the respective intermediate channel 142a-142d, the cut-outs 312a-312d have a greater surface area to channel moisture, fluids, etc. from the user to the respective intermediate channel 142a-142d. The cut-outs 312a-312d extend between the opposed ends 138, 140 of adjacent ones of the sections 132a-132d. The cut-outs 312a-312d also have a width, which is different than, and in this example, less than to the width W2 of the respective intermediate channel 142a-142d. Generally, each of the first ends 316 also extend beyond the perimeter of the sensor base 108 to direct moisture, fluids, etc. away from the physiological characteristic sensor assembly 102.

The coupling system 304 may be used with the physiological characteristic sensor assembly 102 to couple the physiological characteristic sensor assembly 102 to the anatomy of the user, as discussed with regard to the coupling system 104. Briefly, with the physiological characteristic sensor assembly 102 (FIG. 1) assembled, the skin adhesive layer 310 is coupled to the backing layer 308 to form the second adhesive member 306. The cut-outs 312a-312d are defined through the backing layer 308 and the skin adhesive layer 310 via laser cutting, die cutting, etc. The first adhesive member 130 is coupled to the second adhesive member 306, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 310 is coupled to the anatomy or skin of the user. With the medical device 100 coupled to the user, the user may perform their daily activities with increased comfort and breathability as the cut-outs 312a-312d increase the moisture vapor transmission rate. In this regard, the cut-outs 312a-312d enable the moisture, fluids, etc. on the anatomy or skin of a user to escape to the ambient environment, and the main channel 136 and the intermediate channels 142a-142d of the first adhesive member 130 cooperate to direct the moisture, fluids, etc. toward the terminal end 110b of the sensor base 108, which improves breathability of the medical device 100. Moreover, the cut-outs 312a-312d of the second adhesive member 306 provides increased conformity and flexibility of the medical device 100 when coupled to the anatomy of the user by reducing the bonding area of the second adhesive member 306.

Figure 7:
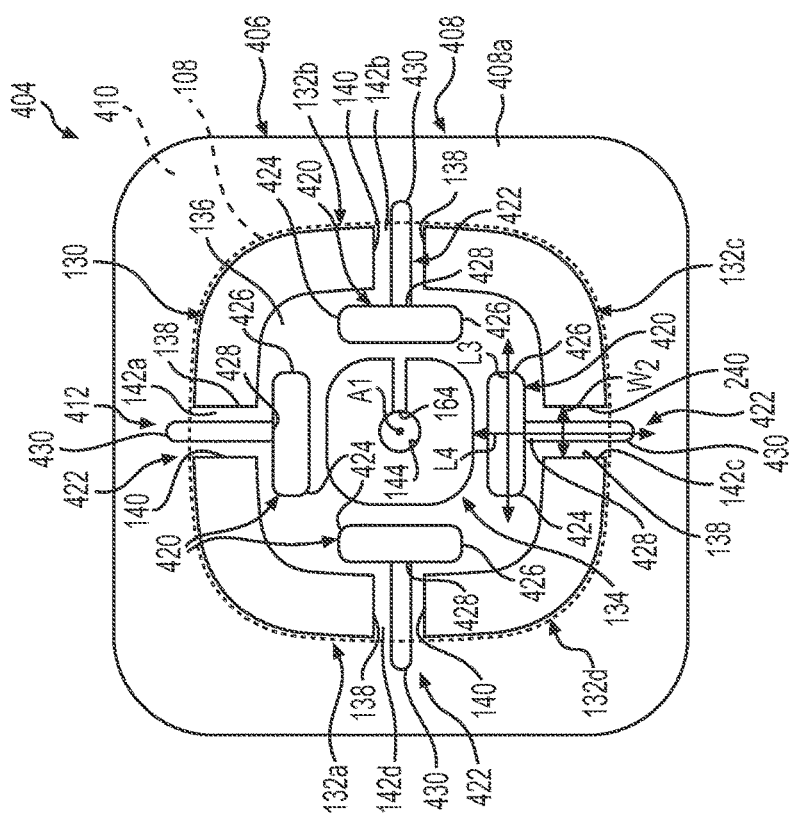
FIG. 7 is a top view of another exemplary coupling system that provides increased breathability for use with the medical device of FIG. 1.

It should be noted that in other embodiments, the coupling system 104 may be configured differently to improve breathability by increasing the moisture vapor transmission rate and directing moisture, fluids, etc. away from the medical device 100. For example, with reference to FIG. 7, a coupling system 404 is shown. As the coupling system 404 includes the same or similar components as the coupling system 104 discussed with regard to FIGS. 1-4, the same reference numerals will be used to denote the same or similar components. FIG. 7 is a schematic top view of the coupling system 404. In this example, the coupling system 404 includes the first adhesive member 130 and a second adhesive member 406. The first adhesive member 130 couples the sensor base 108 to the second adhesive member 406. As discussed, the first adhesive member 130 is a moisture guidance system, which in this example, cooperates with the second adhesive member 406 to further direct moisture, fluids, etc. away from the user and the physiological characteristic sensor assembly 102.

The second adhesive member 406 couples the physiological characteristic sensor assembly 102 (FIG. 1) to the user.

A perimeter of the sensor base 108 of the physiological characteristic sensor assembly 102 is shown in FIG. 7 by a dashed line. In one example, the second adhesive member 406 includes a backing layer 408, a skin adhesive layer 410, the central bore 164 and at least one or a plurality of cut-outs 412. The backing layer 408 and the skin adhesive layer 410 cooperate to define an adhesive skin patch for coupling the physiological characteristic sensor assembly 102 (FIG. 1) to the user. The backing layer 408 is composed of a nonwoven polyurethane, for example. The backing layer 408 has a first surface 408a coupled to the first adhesive member 130, and an opposite second surface coupled to the skin adhesive layer 410. The skin adhesive layer 410 is composed of an acrylic adhesive, which may be painted, coated or otherwise formed on the backing layer 408. One side of the skin adhesive layer 410 is coupled to the backing layer 408, and a second opposite side is configured to be coupled to an anatomy, such as a skin of a user, when the physiological characteristic sensor assembly 102 is deployed on the user. The central bore 164 is coaxially aligned with the central bore 144 of the first adhesive member 130 to enable the glucose sensor 106 to pass through the second adhesive member 406. Thus, the central bore 164 is defined through both the backing layer 408 and the skin adhesive layer 410.

The cut-outs 412 are defined through both the backing layer 408 and the skin adhesive layer 410 such that the cut-outs 412 define areas of the second adhesive member 406 that are devoid of material or are open. The cut-outs 412 enable communication between the anatomy or skin of the user and the coupling system 404, which enables moisture, such as sweat, on the skin of the user to be directed into the ambient environment and away from the physiological characteristic sensor assembly 102. In one example, the second adhesive member 406 defines four cut-outs 412a-412d, however, the second adhesive member 406 may define any number of cut-outs 412. The cut-outs 412a-412d are spaced apart about the first surface 408a of the backing layer 408, and thus, about a perimeter of the second adhesive member 406. In this example, each of the cut-outs 412a-412d is substantially T-shaped; however, the cut-outs 412a-412d may have any desired shape.

Each of the cut-outs 412a-412d has a first portion 420 and a second portion 422. The first portion 420 has a first end 424 opposite a second end 426, and extends along a longitudinal axis L3 from the first end 424 to the second end 426. The second portion 422 has a third end 428 opposite a fourth end 430, and extends along a longitudinal axis L4 from the third end 428 to the fourth end 430. The third end 428 of each second portion 422 is in communication with a respective first portion 420. The longitudinal axes L3 and L4 are each transverse to, and in this example, substantially perpendicular to, the axis A1. The longitudinal axis L3 is transverse to, and in this example, substantially perpendicular to the longitudinal axis L4. In this example, the cut-outs 412a-412d are arranged to be aligned with the main channel 136 and the intermediate channels 142a-142d, and are in communication with the main channel 136 and the intermediate channels 142a-142d of the first adhesive member 130 to promote the transfer of moisture, fluid, etc. from the anatomy of the user to the main channel 136 and the intermediate channels 142a-142d when the first adhesive member 130 is coupled to the second adhesive member 406. The first portion 420 is aligned with the main channel 136, while the second portion 422 is aligned with the respective intermediate channel 142a-142d. The second portion 422 of each of the cut-outs 412a-412d is defined such that each of the second portions 422 extend beyond and across the respective intermediate channel 142a-142d of the first adhesive member 130. By extending beyond the respective intermediate channel 142a-142d, the second portions 422 have a greater surface area to channel moisture, fluids, etc. from the user to the respective intermediate channel 142a-142d. Generally, each of the fourth ends 430 also extend beyond the perimeter of the sensor base 108 to direct moisture, fluids, etc. away from the physiological characteristic sensor assembly 102. The first portion 420 of each of the cut-outs 412a-412d are defined such that each of the first end 424 and the second end 426 extend beyond or across the respective intermediate channel 142a-142d of the first adhesive member 130. Stated another way, the first portion 420 has a length along the longitudinal axis L3, which is greater than the width W2 of the respective intermediate channel 142a-142d. The second portions 422 also have a width, which is different than, and in this example, less than the width W2 of the respective intermediate channel 142a-142d.

The coupling system 404 may be used with the physiological characteristic sensor assembly 102 to couple the physiological characteristic sensor assembly 102 to the anatomy of the user, as discussed with regard to the coupling system 104. Briefly, with the physiological characteristic sensor assembly 102 (FIG. 1) assembled, the skin adhesive layer 410 is coupled to the backing layer 408 to form the second adhesive member 406. The cut-outs 412a-412d are defined through the backing layer 408 and the skin adhesive layer 410 via laser cutting, die cutting, etc. The first adhesive member 130 is coupled to the second adhesive member 406, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 410 is coupled to the anatomy or skin of the user. With the medical device 100 coupled to the user, the user may perform their daily activities with increased comfort and breathability as the cut-outs 412a-412d increase the moisture vapor transmission rate. In this regard, the cut-outs 412a-412d enable the moisture, fluids, etc. on the anatomy or skin of a user to escape to the ambient environment, and the main channel 136 and the intermediate channels 142a-142d of the first adhesive member 130 cooperate to direct the moisture, fluids, etc. toward the terminal end 110b of the sensor base 108, which improves breathability of the medical device 100. Moreover, the cut-outs 412a-412d of the second adhesive member 406 provides increased conformity and flexibility of the medical device 100 when coupled to the anatomy of the user by reducing the bonding area of the second adhesive member 406.

Figure 8:
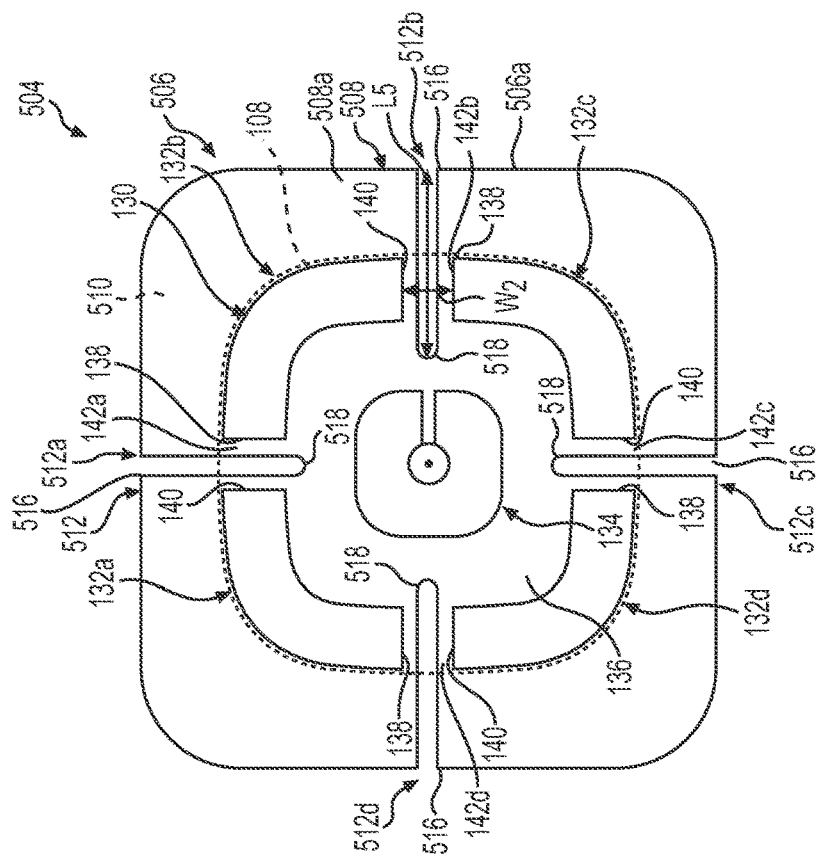
FIG. 8 is a top view of another exemplary coupling system that provides increased breathability for use with the medical device of FIG. 1.

It should be noted that in other embodiments, the coupling system 104 may be configured differently to improve breathability by increasing the moisture vapor transmission rate and directing moisture, fluids, etc. away from the medical device 100. For example, with reference to FIG. 8, a coupling system 504 is shown. As the coupling system 504 includes the same or similar components as the coupling system 104 discussed with regard to FIGS. 1-4, the same reference numerals will be used to denote the same or similar components. FIG. 8 is a schematic top view of the coupling system 504. In this example, the coupling system 504 includes the first adhesive member 130 and a second adhesive member 506. The first adhesive member 130 couples the sensor base 108 to the second adhesive member 506. As discussed, the first adhesive member 130 is a moisture guidance system, which in this example, cooperates with the second adhesive member 506 to further direct moisture, fluids, etc. away from the user and the physiological characteristic sensor assembly 102.

The second adhesive member 506 couples the physiological characteristic sensor assembly 102 (FIG. 1) to the user. A perimeter of the sensor base 108 of the physiological characteristic sensor assembly 102 is shown in FIG. 8 by a dashed line. In one example, the second adhesive member 506 includes a backing layer 508, a skin adhesive layer 510, the central bore 164 and at least one or a plurality of cut-outs 512. The backing layer 508 and the skin adhesive layer 510 cooperate to define an adhesive skin patch for coupling the physiological characteristic sensor assembly 102 (FIG. 1) to the user. The backing layer 508 is composed of a nonwoven polyurethane, for example. The backing layer 508 has a first surface 508*a* coupled to the first adhesive member 130, and an opposite second surface coupled to the skin adhesive layer 510. The skin adhesive layer 510 is composed of an acrylic adhesive, which may be painted, coated or otherwise formed on the backing layer 508. One side of the skin adhesive layer 510 is coupled to the backing layer 508, and a second opposite side is configured to be coupled to an anatomy, such as a skin of a user, when the physiological characteristic sensor assembly 102 is deployed on the user. The central bore 164 is coaxially aligned with the central bore 144 of the first adhesive member 130 to enable the glucose sensor 106 to pass through the second adhesive member 506. Thus, the central bore 164 is defined through both the backing layer 508 and the skin adhesive layer 510.

The cut-outs 512 are defined through both the backing layer 508 and the skin adhesive layer 510 such that the cut-outs 512 define areas of the second adhesive member 506 that are devoid of material or are open. The cut-outs 512 enable communication between the anatomy or skin of the user and the coupling system 504, which enables moisture, such as sweat, on the skin of the user to be directed into the ambient environment and away from the physiological characteristic sensor assembly 102. In one example, the second adhesive member 506 defines four cut-outs 512*a*-512*d*, however, the second adhesive member 506 may define any number of cut-outs 512. The cut-outs 512*a*-512*d* are spaced apart about the first surface 508*a* of the backing layer 508, and thus, about a perimeter of the second adhesive member 506. In this example, each of the cut-outs 512*a*-512*d* is oblong, discorectangle or stadium in shape; however, the cut-outs 512*a*-512*d* may have any desired shape.

Each of the cut-outs 512*a*-512*d* has a first end 516 opposite a second end 518, and extend along a longitudinal axis L5 from the first end 516 to the second end 518. The longitudinal axis L5 is transverse to, and in this example, substantially perpendicular to, the axis A1. In this example, the cut-outs 512*a*-512*d* are arranged to be aligned with the intermediate channels 142*a*-142*d* and are in communication with the intermediate channels 142*a*-142*d* of the first adhesive member 130 to promote the transfer of moisture, fluid, etc. from the anatomy of the user to the intermediate channels 142*a*-142*d* when the first adhesive member 130 is coupled to the second adhesive member 506. The cut-outs 512*a*-512*d* are defined such that each of the first end 516 and the second end 518 extend beyond or across the respective intermediate channel 142*a*-142*d* of the first adhesive member 130. Stated another way, each of the cut-outs 512*a*-512*d* has a length along the longitudinal axis L5, which is greater than the width W2 of the respective intermediate channel 142*a*-142*d*. The cut-outs 512*a*-512*d* also have a width, which is different than, and in this example, less than the width W2 of the respective intermediate channel 142*a*-142*d*. By extending beyond the respective intermediate channel 142*a*-142*d*, the cut-outs 512*a*-512*d* have a greater surface area to channel moisture, fluids, etc. from the user to the respective intermediate channel 142*a*-142*d*. The cut-outs 512*a*-512*d* extend between the opposed ends 138, 140 of adjacent ones of the sections 132*a*-132*d*. Generally, each of the first ends 516 also extend beyond the perimeter of the sensor base 108 to a terminal edge 506*a* of the second adhesive member 506 to direct moisture, fluids, etc. away from the medical device 100.

The coupling system 504 may be used with the physiological characteristic sensor assembly 102 to couple the physiological characteristic sensor assembly 102 to the anatomy of the user, as discussed with regard to the coupling system 104. Briefly, with the physiological characteristic sensor assembly 102 (FIG. 1) assembled, the skin adhesive layer 510 is coupled to the backing layer 508 to form the second adhesive member 506. The cut-outs 512*a*-512*d* are defined through the backing layer 508 and the skin adhesive layer 510 via laser cutting, die cutting, etc. The first adhesive member 130 is coupled to the second adhesive member 506, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 510 is coupled to the anatomy or skin of the user. With the medical device 100 coupled to the user, the user may perform their daily activities with increased comfort and breathability as the cut-outs 512*a*-512*d* increase the moisture vapor transmission rate. In this regard, the cut-outs 512*a*-512*d* enable the moisture, fluids, etc. on the anatomy or skin of a user to escape to the ambient environment and to be directed beyond the terminal edge 506*a* of the second adhesive member 506, and the main channel 136 and the intermediate channels 142*a*-142*d* of the first adhesive member 130 cooperate to direct the moisture, fluids, etc. toward the terminal end 110*b* of the sensor base 108, which improves breathability of the medical device 100. Moreover, the cut-outs 512*a*-512*d* of the second adhesive member 506 provide increased conformity and flexibility of the medical device 100 when coupled to the anatomy of the user by reducing the bonding area of the second adhesive member 506.

Figure 9:
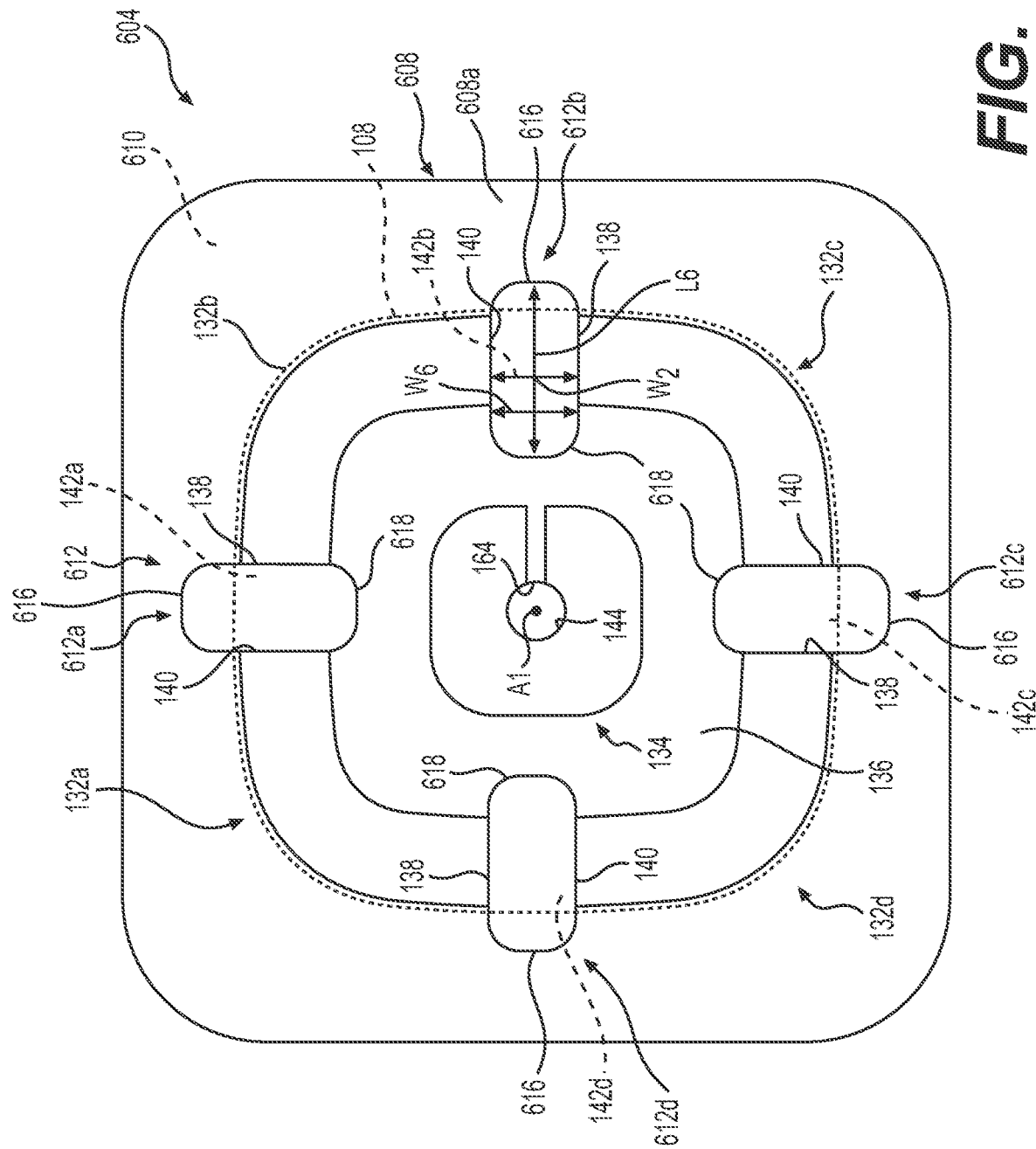
FIG. 9 is a top view of another exemplary coupling system that provides increased breathability for use with the medical device of FIG. 1.

It should be noted that in other embodiments, the coupling system 104 may be configured differently to improve breathability by increasing the moisture vapor transmission rate and directing moisture, fluids, etc. away from the medical device 100. For example, with reference to FIG. 9, a coupling system 604 is shown. As the coupling system 604 includes the same or similar components as the coupling system 104 discussed with regard to FIGS. 1-4, the same reference numerals will be used to denote the same or similar components. FIG. 9 is a schematic top view of the coupling system 604. In this example, the coupling system 604 includes the first adhesive member 130 and a second adhesive member 606. The first adhesive member 130 couples the sensor base 108 to the second adhesive member 606. As discussed, the first adhesive member 130 is a moisture guidance system, which in this example, cooperates with the second adhesive member 606 to further direct moisture, fluids, etc. away from the user and the physiological characteristic sensor assembly 102.

The second adhesive member 606 couples the physiological characteristic sensor assembly 102 (FIG. 1) to the user. A perimeter of the sensor base 108 of the physiological characteristic sensor assembly 102 is shown in FIG. 9 by a dashed line. In one example, the second adhesive member 606 includes a backing layer 608, a skin adhesive layer 610, the central bore 164 and at least one or a plurality of cut-outs 612. The backing layer 608 and the skin adhesive layer 610 cooperate to define an adhesive skin patch for coupling the physiological characteristic sensor assembly 102 (FIG. 1) to the user. The backing layer 608 is composed of a nonwoven polyurethane, for example. The backing layer 608 has a first surface 608a coupled to the first adhesive member 130, and an opposite second surface coupled to the skin adhesive layer 610. The skin adhesive layer 610 is composed of an acrylic adhesive, which may be painted, coated or otherwise formed on the backing layer 608. One side of the skin adhesive layer 610 is coupled to the backing layer 608, and a second opposite side is configured to be coupled to an anatomy, such as a skin of a user, when the physiological characteristic sensor assembly 102 is deployed on the user. The central bore 164 is coaxially aligned with the central bore 144 of the first adhesive member 130 to enable the glucose sensor 106 to pass through the second adhesive member 606. Thus, the central bore 164 is defined through both the backing layer 608 and the skin adhesive layer 610.

The cut-outs 612 are defined through both the backing layer 608 and the skin adhesive layer 610 such that the cut-outs 612 define areas of the second adhesive member 606 that are devoid of material or are open. The cut-outs 612 enable communication between the anatomy or skin of the user and the coupling system 604, which enables moisture, such as sweat, on the skin of the user to be directed into the ambient environment and away from the physiological characteristic sensor assembly 102. In one example, the second adhesive member 606 defines four cut-outs 612a-612d, however, the second adhesive member 606 may define any number of cut-outs 612. The cut-outs 612a-612d are spaced apart about the first surface 608a of the backing layer 608, and thus, about a perimeter of the second adhesive member 606. In this example, each of the cut-outs 612a-612d is oblong, discorectangle or stadium in shape; however, the cut-outs 612a-612d may have any desired shape Each of the cut-outs 612a-612d has a first end 616 opposite a second end 618, and extend along a longitudinal axis L6 from the first end 616 to the second end 618. The longitudinal axis L6 is transverse to, and in this example, substantially perpendicular to, the axis A1. In this example, the cut-outs 612a-612d are arranged to be aligned with the intermediate channels 142a-142d and in this example, each of the cut-outs 612a-612d are defined to encompass an entirety of the intermediate channels 142a-142d. Stated another way, each of the cut-outs 612a-612d is collinear with a respective one of the intermediate channels 142a-142d. The cut-outs 612a-612d are in communication with the main channel 136 of the first adhesive member 130 when the first adhesive member 130 is coupled to the second adhesive member 606 to promote the transfer of moisture, fluid, etc. from the anatomy of the user to the ambient environment and away from the sensor base 108. The cut-outs 612a-612d are defined such that each of the first end 616 and the second end 618 extend beyond the respective intermediate channel 142a-142d of the first adhesive member 130. The cut-outs 612a-612d also have a width W6, which is equal to the width W2 of the respective intermediate channel 142a-142d. By extending beyond and encompassing the respective intermediate channel 142a-142d, the cut-outs 612a-612d have a greater surface area to channel moisture, fluids, etc. from the user to the respective intermediate channel 142a-142d. The cut-outs 612a-612d are arranged to be defined between the opposed ends 138, 140 of adjacent ones of the sections 132a-132d. Generally, each of the first ends 616 also extend beyond the perimeter of the sensor base 108 to direct moisture, fluids, etc. away from the physiological characteristic sensor assembly 102.

The coupling system 604 may be used with the physiological characteristic sensor assembly 102 to couple the physiological characteristic sensor assembly 102 to the anatomy of the user, as discussed with regard to the coupling system 104. Briefly, with the physiological characteristic sensor assembly 102 (FIG. 1) assembled, the skin adhesive layer 610 is coupled to the backing layer 608 to form the second adhesive member 606. The cut-outs 612a-612d are defined through the backing layer 608 and the skin adhesive layer 610 via laser cutting, die cutting, etc. The first adhesive member 130 is coupled to the second adhesive member 606, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 610 is coupled to the anatomy or skin of the user. With the medical device 100 coupled to the user, the user may perform their daily activities with increased comfort and breathability as the cut-outs 612a-612d increase the moisture vapor transmission rate. In this regard, the cut-outs 612a-612d enable the moisture, fluids, etc. on the anatomy or skin of a user to escape to the ambient environment and to be directed beyond the perimeter of the sensor base 108, and the main channel 136 and the intermediate channels 142a-142d of the first adhesive member 130 cooperate to direct the moisture, fluids, etc. toward the perimeter of the sensor base 108, which improves breathability of the medical device 100. Moreover, the cut-outs 612a-612d of the second adhesive member 606 provide increased conformity and flexibility of the medical device 100 when coupled to the anatomy of the user by reducing the bonding area of the second adhesive member 606.

Figure 10:
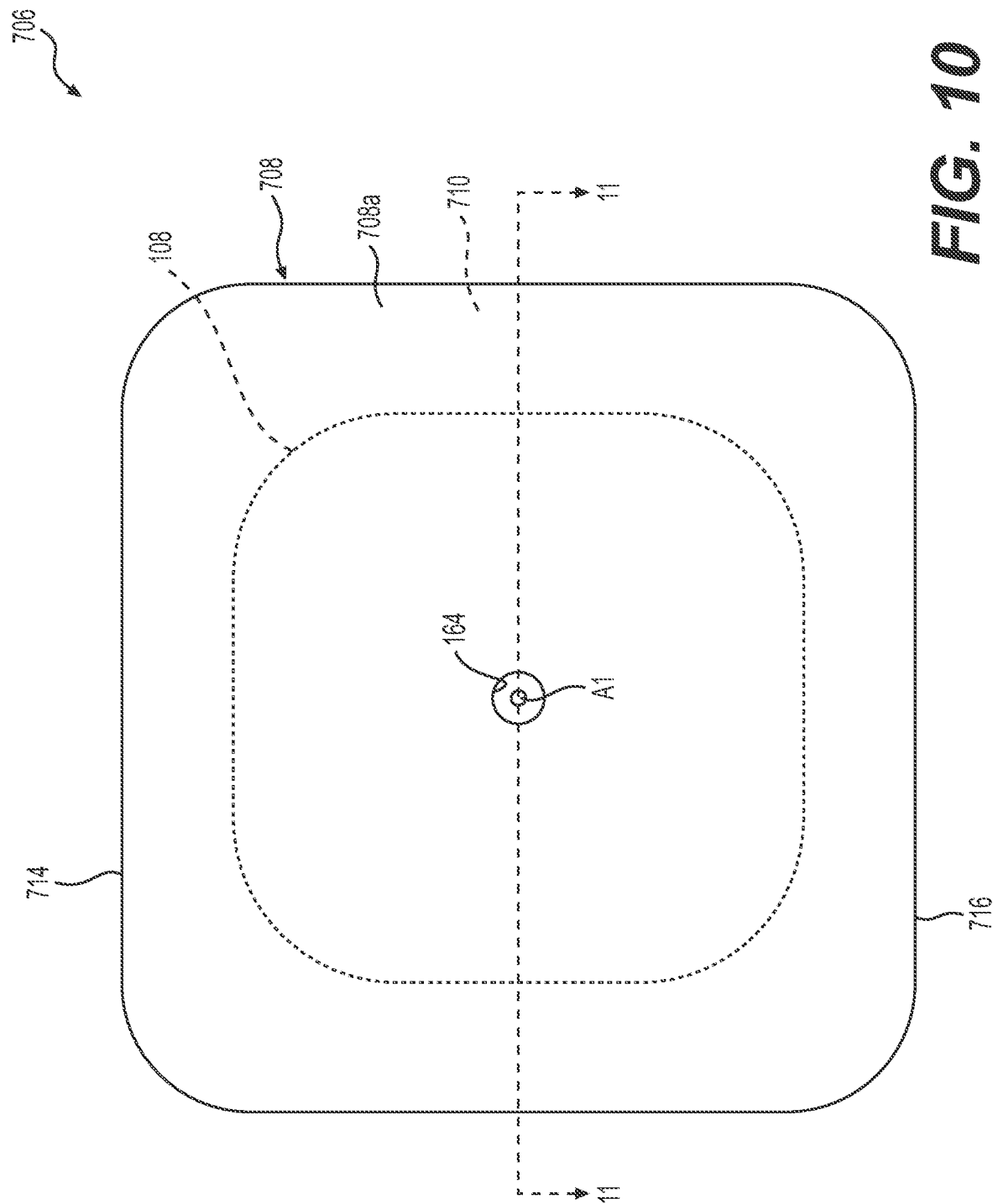
FIG. 10 is a top view of an exemplary second adhesive member of a coupling system that provides increased breathability for use with the medical device of FIG. 1.

It should be noted that in other embodiments, the second adhesive member 131 may be configured differently to improve breathability by increasing the moisture vapor transmission rate and directing moisture, fluids, etc. away from the medical device 100. For example, with reference to FIG. 10, a second adhesive member 706 is shown. As the second adhesive member 706 includes the same or similar components as the second adhesive member 131 discussed with regard to FIGS. 1-4, the same reference numerals will be used to denote the same or similar components. FIG. 10 is a schematic top view of the second adhesive member 706. The second adhesive member 706 couples the physiological characteristic sensor assembly 102 (FIG. 1) to the user. A perimeter of the sensor base 108 of the physiological characteristic sensor assembly 102 is shown in FIG. 10 by a dashed line.

In this example, with reference to FIG. 11, the second adhesive member 706 includes a backing layer 708, a skin adhesive layer 710 and the central bore 164. The backing layer 708 and the skin adhesive layer 710 cooperate to define an adhesive skin patch for coupling the physiological characteristic sensor assembly 102 (FIG. 1) to the user. The backing layer 708 is composed of a nonwoven polyurethane, for example. The backing layer 708 has a first surface 708*a* coupled to the first adhesive member 130 (or the first adhesive member 130'), and an opposite second surface 708*b* coupled to the skin adhesive layer 710. The skin adhesive layer 710 is composed of an acrylic adhesive, which may be painted, coated or otherwise formed on the backing layer 708. A first side 710*a* of the skin adhesive layer 710 is coupled to the backing layer 708, and an opposite second side 710*b* is configured to be coupled to an anatomy, such as a skin of a user, when the physiological characteristic sensor assembly 102 is deployed on the user. The central bore 164 is coaxially aligned with the central bore 144 of the first adhesive member 130 (FIG. 3) to enable the glucose sensor 106 to pass through the second adhesive member 706. Thus, the central bore 164 is defined through both the backing layer 708 and the skin adhesive layer 710.

In this example, the skin adhesive layer 710 is a moisture guidance system and defines a plurality of cut-outs 712. The cut-outs 712 act as channels that enable moisture, such as sweat, fluids, etc., on the skin of the user to be directed away from the physiological characteristic sensor assembly 102 into the ambient environment. In one example, the skin adhesive layer 710 defines four cut-outs 712*a*-712*d*, however, the skin adhesive layer 710 may define any number of cut-outs 712. The cut-outs 712*a*-712*d* are spaced apart about a width W7 of the skin adhesive layer 710, and each of the cut-outs 712*a*-712*d* have a width W8. In one example, the cut-outs 712*a*-712*d* result in the second side 710*b* of the skin adhesive layer 710 defining a plurality of surfaces 713 that contact a skin of the user when the physiological characteristic sensor assembly 102 is coupled to the user. In one example, the surfaces 713 define at least about 25% or greater of the second side 710*b*. Generally, with brief reference to FIG. 10, the cut-outs 712*a*-712*d* are defined through the skin adhesive layer 710 to extend from a first side 714 of the skin adhesive layer 710 to an opposite second side 716 of the skin adhesive layer 710. In this example, with reference to FIG. 11, each of the cut-outs 712*a*-712*d* has a rectangular cross-sectional shape; however, the cut-outs 712*a*-712*d* may have any desired cross-sectional shape, including, but not limited to triangular, semi-circular, etc. The cut-outs 712 are defined through an entirety of the skin adhesive layer 710 from the first side 710*a* to the second side 710*b* such that the cut-outs 712 define areas of the skin adhesive layer 710 that are devoid of material or are open.

It should be noted, however, that while the cut-outs 712*a*-712*d* are shown in FIG. 11 as extending through the skin adhesive layer 710 from the first side 710*a* to the second side 710*b*, the cut-outs 712*a*-712*d* may be defined to extend through only a portion of the skin adhesive layer 710. For example, with reference to FIG. 12, cut-outs 712*a'*-712*d'* are shown to extend from the second side 710*b* toward the first side 710*a* at a predetermined depth D. In the example of FIG. 12, the cut-outs 712*a'*-712*d'* extend through only a portion of a thickness T of the skin adhesive layer 710. In one example, the cut-outs 712*a'*-712*d'* may have a depth D of about 50% to about 75% the thickness T of the skin adhesive layer 710. In this example, the cut-outs 712*a'*-712*d'* have a triangular cross-sectional shape, however, the cut-outs 712*a'*-712*d'* may have any desired cross-sectional shape, including, but not limited to rectangular, square, semi-circular, etc. In one example, the cut-outs 712*a'*-712*d'* result in the second side 710*b* of the skin adhesive layer 710 having a plurality of surfaces 713' that contact a skin of the user when the physiological characteristic sensor assembly 102 is coupled to the user. In one example, the surfaces 713' define at least about 25% or greater of the second side 710*b*.

The second adhesive member 706 may be used with the coupling system 104 to couple the physiological characteristic sensor assembly 102 to the anatomy of the user. Briefly, with the physiological characteristic sensor assembly 102 (FIG. 1) assembled, the cut-outs 712*a*-712*d* or 712*a'*-712*d'* are defined through the skin adhesive layer 710. In one example, the cut-outs 712*a*-712*d* are defined via masking the backing layer 708, for example, to inhibit the application of the skin adhesive layer 710 along the backing layer 708 at the respective cut-out 712*a*-712*d*. Alternatively, the skin adhesive layer 710 may be screen printed onto the backing layer 708 to define the cut-outs 712*a*-712*d*. As a further alternative, the skin adhesive layer 710 may be laser cut to define the cut-outs 712*a*-712*d*. Further, the skin adhesive layer 710 may be molded onto the backing layer 708 to define the cut-outs 712*a*-712*d*. The skin adhesive layer 710 is then coupled to or defined on the backing layer 708 to form the second adhesive member 706. Alternatively, the skin adhesive layer 710 is coupled to or defined on the backing layer 708 and the cut-outs 712*a'*-712*d'* are defined via molding. With the second adhesive member 706 formed, the first adhesive member 130 is coupled to the second adhesive member 706, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 710 is coupled to the anatomy or skin of the user. With the medical device 100 coupled to the user, the user may perform their daily activities with increased comfort and breathability as the cut-outs 712*a*-712*d* increase the moisture vapor transmission rate. In this regard, the cut-outs 712*a*-712*d* and 712*a'*-712*d'* enable the moisture, fluids, etc. on the anatomy or skin of a user to escape to the ambient environment, which improves breathability of the medical device 100. Moreover, the cut-outs 712*a*-712*d* and 712*a'*-712*d'* of the skin adhesive layer 710 provides increased conformity and flexibility of the medical device 100 when coupled to the anatomy of the user by reducing the bonding area of the skin adhesive layer 710.

Figure 13:
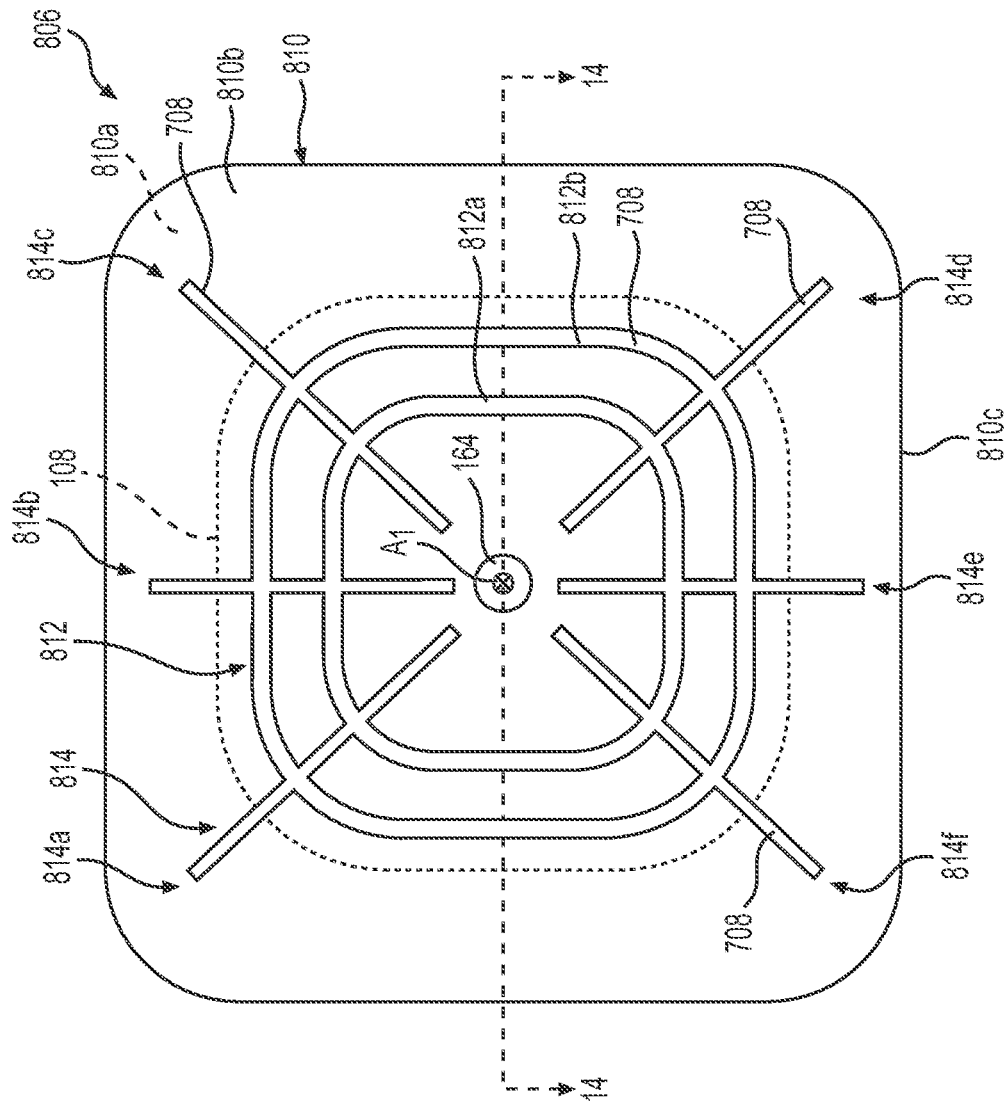
FIG. 13 is a bottom view of an exemplary second adhesive member of a coupling system that provides increased breathability for use with the medical device of FIG. 1.

It should be noted that in other embodiments, the second adhesive member 131 may be configured differently to improve breathability by increasing the moisture vapor transmission rate and directing moisture, fluids, etc. away from the medical device 100. For example, with reference to FIG. 13, a second adhesive member 806 is shown. As the second adhesive member 806 includes the same or similar components as the second adhesive member 131 discussed with regard to FIGS. 1-4 and the second adhesive member 706 discussed with regard to FIGS. 10-12, the same reference numerals will be used to denote the same or similar components. FIG. 13 is a schematic bottom view of the second adhesive member 806. The second adhesive member 806 couples the physiological characteristic sensor assembly 102 (FIG. 1) to the user. A perimeter of the sensor base 108 of the physiological characteristic sensor assembly 102 is shown in FIG. 13 by a dashed line.

Figure 14:
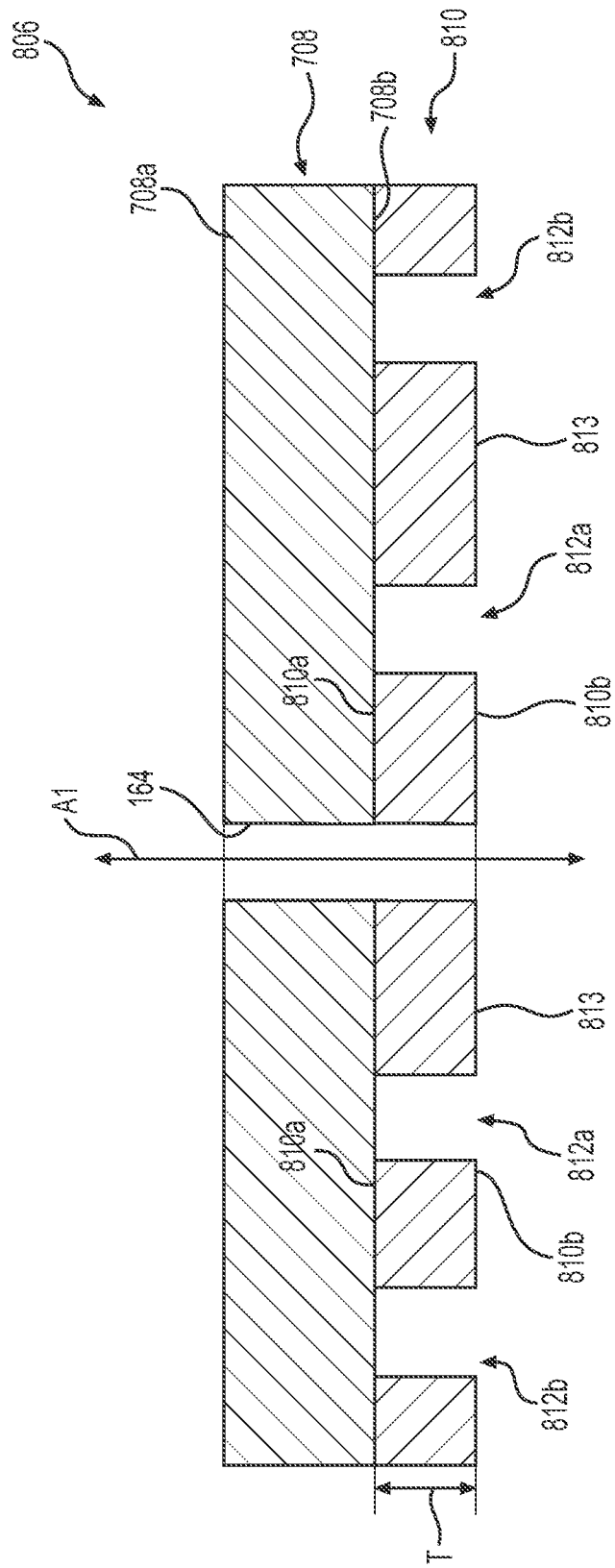
FIG. 14 is a cross-sectional view of the second adhesive member of FIG. 13, taken along line 14-14 of FIG. 13.

In this example, with reference to FIG. 14, the second adhesive member 806 includes the backing layer 708, a skin adhesive layer 810 and the central bore 164. The backing layer 708 and the skin adhesive layer 810 cooperate to define an adhesive skin patch for coupling the physiological characteristic sensor assembly 102 (FIG. 1) to the user. As discussed, the backing layer 708 is composed of a nonwoven polyurethane, for example, and has the first surface 708*a* coupled to the first adhesive member 130 (or the first adhesive member 130'), and the opposite second surface 708*b* coupled to the skin adhesive layer 810. The skin adhesive layer 810 is composed of an acrylic adhesive, which may be painted, coated or otherwise formed on the backing layer 708. A first side 810*a* of the skin adhesive layer 810 is coupled to the backing layer 708, and an opposite second side 810*b* is configured to be coupled to an anatomy, such as a skin of a user, when the physiological characteristic sensor assembly 102 is deployed on the user. The central bore 164 is coaxially aligned with the central bore 144 of the first adhesive member 130 (FIG. 3) to enable the glucose sensor 106 to pass through the second adhesive member 806. Thus, the central bore 164 is defined through both the backing layer 708 and the skin adhesive layer 810.

In this example, the skin adhesive layer 810 is a moisture guidance system and defines a plurality of cut-outs 812, 814. The cut-outs 812, 814 act as channels that enable moisture, such as sweat, fluids, etc., on the skin of the user to be directed away from the physiological characteristic sensor assembly 102 into the ambient environment. In one example, with reference back to FIG. 13, the skin adhesive layer 810 defines at least one or a plurality of hub cut-outs 812 and at least one or a plurality of spoke cut-outs 814. In this example, the skin adhesive layer 810 defines two hub cut-outs 812*a*, 812*b*, which are spaced apart from each other and concentric with the axis A1. It should be noted, however, that the skin adhesive layer 810 may include any number of hub cut-outs 812*a*-812*b*. The hub cut-outs 812*a*-812*b* are generally defined through the skin adhesive layer 810 so as to be contained within the perimeter of the sensor base 108 when the sensor base 108 is coupled to the second adhesive member 806. With reference back to FIG. 14, the hub cut-outs 812*a*-812*b* have a rectangular cross-sectional shape; however, the hub cut-outs 812*a*-812*b* may have any desired cross-sectional shape, including, but not limited to triangular, semi-circular, etc. In this example, the hub cut-outs 812*a*-812*b* are defined through an entirety of the skin adhesive layer 810 from the first side 810*a* to the second side 810*b* such that the hub cut-outs 812*a*-812*b* define areas of the skin adhesive layer 810 that are devoid of material or are open. It should be noted, however, that while the hub cut-outs 812*a*-812*b* are shown in FIG. 14 as extending through the skin adhesive layer 810 from the first side 810*a* to the second side 810*b*, the hub cut-outs 812*a*-812*b* may be defined to extend through only a portion of the skin adhesive layer 810 to a predetermined depth.

With reference back to FIG. 13, in this example, the skin adhesive layer 810 defines six spoke cut-outs 814*a*-814*f*, which are spaced apart from each other about the axis A1. It should be noted, however, that the skin adhesive layer 810 may include any number of spoke cut-outs 814. The spoke cut-outs 814*a*-814*f* are generally defined through the skin adhesive layer 810 so as to extend from proximate the central bore 164 outwardly toward a perimeter 810*c* of the skin adhesive layer 810. Generally, the spoke cut-outs 814*a*-814*f* are spaced apart from the central bore 164 and the perimeter 810*c*; however, the spoke cut-outs 814*a*-814*f* may extend to the perimeter 810*c*, if desired. Each of the spoke cut-outs 814*a*-814*f* intersect the hub cut-outs 812*a*-812*b* to assist in guiding moisture, fluids, etc. from the hub cut-outs 812*a*-812*b* toward the perimeter 810*c*. In this example, two of the spoke cut-outs 814*b*, 814*d* extend along an axis substantially perpendicular to the axis A1, while the remainder of the spoke cut-outs 814*a*, 814*c*, 814*d*, 814*f* extend along an axis transverse to the axis A1. The spoke cut-outs 814*a*-814*f* have a rectangular cross-sectional shape; however, the spoke cut-outs 814*a*-814*f* may have any desired cross-sectional shape, including, but not limited to triangular, semi-circular, etc. In this example, the spoke cut-outs 814*a*-814*f* are defined through an entirety of the skin adhesive layer 810 such that the backing layer 708 is exposed (the spoke cut-outs 814*a*-814*f* extend through the skin adhesive layer 810 from the first side 810*a* to the second side 810*b* (FIG. 14)) and the spoke cut-outs 814*a*-814*f* define areas of the skin adhesive layer 810 that are devoid of material or are open. It should be noted, however, that while the spoke cut-outs 814*a*-814*f* are shown in FIG. 13 as extending through the skin adhesive layer 810 to the backing layer 708, the spoke cut-outs 814*a*-814*f* may be defined to extend through only a portion of the skin adhesive layer 810 to a predetermined depth. In one example, the hub cut-outs 812*a*-812*b* and the spoke cut-outs 814*a*-814*f* result in the second side 810*b* of the skin adhesive layer 810 defining a plurality of surfaces 813 that contact a skin of the user when the physiological characteristic sensor assembly 102 is coupled to the user. In one example, the surfaces 813 define at least about 25% or greater of the second side 710*b*.

The second adhesive member 806 may be used with the coupling system 104 to couple the physiological characteristic sensor assembly 102 to the anatomy of the user. Briefly, with the physiological characteristic sensor assembly 102 (FIG. 1) assembled, the hub cut-outs 812*a*-812*b* and the spoke cut-outs 814*a*-814*f* are defined through the skin adhesive layer 810. In one example, the hub cut-outs 812*a*-812*b* and the spoke cut-outs 814*a*-814*f* are defined via masking the backing layer 708, for example, to inhibit the application of the skin adhesive layer 810 along the backing layer 708 at the respective cut-out 812, 814. Alternatively, the skin adhesive layer 810 may be screen printed onto the backing layer 708 to define hub cut-outs 812*a*-812*b* and the spoke cut-outs 814*a*-814*f*. The skin adhesive layer 810 is then coupled to or defined on the backing layer 708 to form the second adhesive member 806. Alternatively, the skin adhesive layer 810 is coupled to or defined on the backing layer 708 and the hub cut-outs 812*a*-812*b* and the spoke cut-outs 814*a*-814*f* are defined via molding. With the second adhesive member 804 formed, the first adhesive member 130 is coupled to the second adhesive member 804, and is coupled to the sensor base 108. With the medical device 100 assembled, the medical device 100 may be coupled to a sensor inserter (not shown), packaged, sterilized and shipped to an end user.

Once received, the user may remove the packaging to expose the medical device 100. The user may manipulate the sensor inserter to deploy the physiological characteristic sensor assembly 102 onto the user such that the glucose sensor 106 (FIG. 1) is positioned within a tissue of the user and the skin adhesive layer 810 is coupled to the anatomy or skin of the user. With the medical device 100 coupled to the user, the user may perform their daily activities with increased comfort and breathability as the hub cut-outs 812*a*-812*b* and the spoke cut-outs 814*a*-814*f* increase the moisture vapor transmission rate. In this regard, the hub cut-outs 812*a*-812*b* and the spoke cut-outs 814*a*-814*f* enable the moisture, fluids, etc. on the anatomy or skin of a user to escape to the ambient environment, which improves breathability of the medical device 100. Moreover, the hub cut-outs 812*a*-812*b* and the spoke cut-outs 814*a*-814*f* of the skin adhesive layer 810 provide increased conformity and flexibility of the medical device 100 when coupled to the anatomy of the user by reducing the bonding area of the skin adhesive layer 810.

It should be noted that in other embodiments, a medical device may be configured differently for use with a moisture guidance system defined by a first adhesive member. With reference to FIG. 15, a medical device 900 is shown. In this example, the medical device 900 includes a physiological characteristic sensor assembly 902 and a coupling system 904. It should be noted that in certain embodiments, the physiological characteristic sensor assembly 902 may comprise the physiological characteristic sensor assembly 10 described in commonly assigned U.S. application Ser. No. 16/392,527 to Garai, et al., filed on Apr. 23, 2019 and titled "Flexible Physiological Characteristic Sensor Assembly," the relevant portion of which is incorporated herein by reference. Generally, the physiological characteristic sensor assembly 902 and the coupling system 904 are coupled together as a single unit. The physiological characteristic sensor assembly 902 and the coupling system 904 may be packaged together for use by a consumer.

Certain features, aspects, and characteristics of the physiological characteristic sensor assembly 902 are discussed in U.S. application Ser. No. 16/392,527, previously incorporated herein, and, as such, will not be described in detail here. Briefly, the physiological characteristic sensor assembly 902 can be pre-connected as part of a sensor set, which could also include a flexible sensor electronics module (not shown), such as a wireless transmitter that communicates with an infusion pump, a monitor device, or the like, which connects to the physiological characteristic sensor assembly 902 after the insertion or deployment of a portion of the physiological characteristic sensor assembly 902 in the body of the user. In one example, the physiological characteristic sensor assembly 902 includes a glucose sensor 906 and a flexible sensor base 908. It should be noted that the physiological characteristic sensor assembly 902 is not limited to a continuous glucose monitor, but rather, various other physiological characteristic sensors may be employed. The glucose sensor 906 may be coupled to the sensor base 908. The glucose sensor 906 is an electrochemical sensor that includes the glucose oxidase enzyme, as is well understood by those familiar with glucose sensor technology. The glucose oxidase enzyme enables the glucose sensor 906 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, the glucose sensor 906 is positionable in subcutaneous tissue of the user by an insertion needle of a sensor inserter to measure the glucose oxidase enzyme.

The sensor base 908 is coupled to the coupling system 904. The sensor base 908 may also feature electrical and physical interfaces and elements that accommodate the sensor electronics module, such as the wireless transmitter that communicates with the infusion pump, the monitor device, or the like. In certain embodiments, the sensor base 908 is composed at least in part from a flexible plastic material.

The coupling system 904 includes a first adhesive member 930 and a second adhesive member 932. The first adhesive member 930 couples the flexible sensor base 908 to the second adhesive member 932. In this example, the first adhesive member 930 is a double-sided pressure sensitive adhesive, which defines a central bore 931 to enable the glucose sensor 906 to pass through the first adhesive member 930. In one example, the first adhesive member 930 is composed of a synthetic rubber, acrylic-based adhesive or a non-woven polyester tape. In one example, the first adhesive member 930 is a moisture guidance system. Thus, in this example, the first adhesive member 930 is defined to direct moisture, fluids, etc. away from the physiological characteristic sensor assembly 902. With reference to FIGS. 16A-16F, the first adhesive member 930 is shown in greater detail.

Figure 16A:
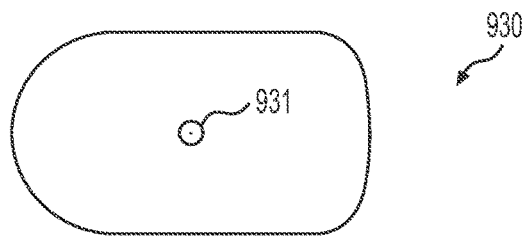
FIGS. 16A-16F are each top views of an exemplary first adhesive member that provides increased breathability for use with the medical device of FIG. 15.
Figure 16B:
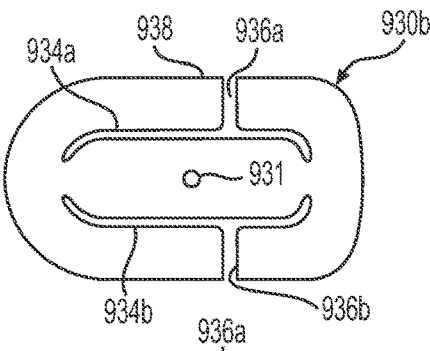

In the example of FIG. 16A, the first adhesive member 930 is substantially continuous, and devoid of any areas of removed material. Thus, in the example of FIG. 16A, the first adhesive member 930 has 100% surface area for coupling between the sensor base 908 and the second adhesive member 932 (FIG. 15). In the example of FIG. 16B, a first adhesive member 930*b* is shown. The first adhesive member 930*b* includes a first cut-out 934*a* opposite a second cut-out 934*b*, and a pair of slits 936*a*-936*b*. The first cut-out 934*a*, the second cut-out 934*b* and the pair of slits 936*a*-936*b* cooperate to direct moisture, fluids, etc. from near the center of the physiological characteristic sensor assembly 902 (FIG. 15) toward a perimeter 938 of the first adhesive member 930*b*. This also imparts breathability to the first adhesive member 930*b*. In the example of FIG. 16B, the first adhesive member 930*b* has about 90% surface area remaining for coupling between the sensor base 908 and the second adhesive member 932.

Figure 16C:
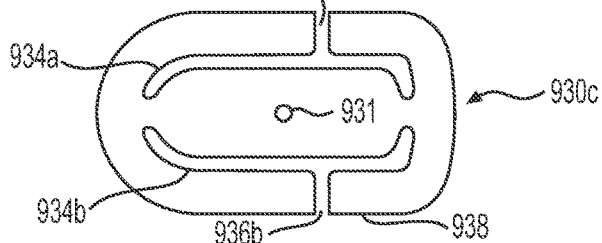

In the example of FIG. 16C, a first adhesive member 930*c* is shown. The first adhesive member 930*c* includes the first cut-out 934*a* opposite the second cut-out 934*b*, and the pair of slits 936*a*-936*b*, although in this example, the first cut-out 934*a*, the second cut-out 934*b* and the pair of slits 936*a*-936*b* have an increased surface area such that an additional amount of the first adhesive member 930*c* is removed. The first cut-out 934*a*, the second cut-out 934*b* and the pair of slits 936*a*-936*b* cooperate to direct moisture, fluids, etc. from near the center of the physiological characteristic sensor assembly 902 (FIG. 15) toward the perimeter 938 of the first adhesive member 930*c*. This also imparts breathability to the first adhesive member 930*c*. In the example of FIG. 16C, the first adhesive member 930*c* has about 80% surface area remaining for coupling between the sensor base 908 and the second adhesive member 932.

Figure 16D:
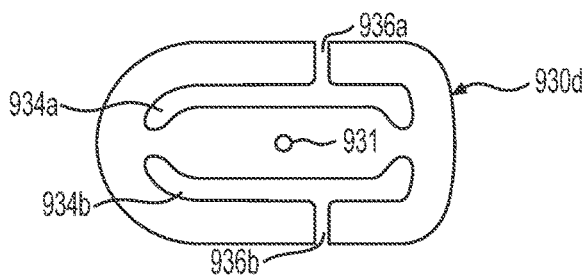

In the example of FIG. 16D, a first adhesive member 930*d* is shown. The first adhesive member 930*d* includes the first cut-out 934*a* opposite the second cut-out 934*b*, and the pair of slits 936*a*-936*b*, although in this example, the first cut-out 934*a*, the second cut-out 934*b* and the pair of slits 936*a*-936*b* have an increased surface area over that of FIG. 16C such that an additional amount of the first adhesive member 930*d* is removed. The first cut-out 934*a*, the second cut-out 934*b* and the pair of slits 936*a*-936*b* cooperate to direct moisture, fluids, etc. from near the center of the physiological characteristic sensor assembly 902 (FIG. 15) toward the perimeter 938 of the first adhesive member 930*d*. This also imparts breathability to the first adhesive member 930*d*. In the example of FIG. 16D, the first adhesive member 930*d* has about 70% surface area remaining for coupling between the sensor base 908 and the second adhesive member 932.

Figure 16E:
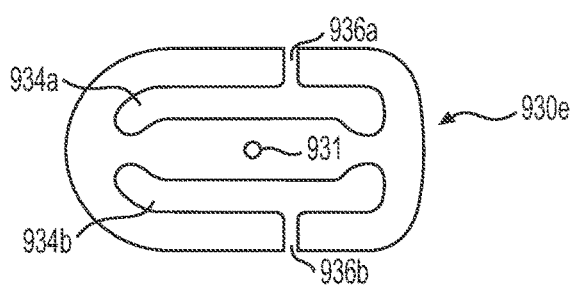

In the example of FIG. 16E, a first adhesive member 930*e* is shown. The first adhesive member 930*e* includes the first cut-out 934*a* opposite the second cut-out 934*b*, and the pair of slits 936*a*-936*b*, although in this example, the first cut-out 934*a*, the second cut-out 934*b* and the pair of slits 936*a*-936*b* have an increased surface area over that of FIG. 16D such that an additional amount of the first adhesive member 930*e* is removed. The first cut-out 934*a*, the second cut-out 934*b* and the pair of slits 936*a*-936*b* cooperate to direct moisture, fluids, etc. from near the center of the physiological characteristic sensor assembly 902 (FIG. 15) toward the perimeter 938 of the first adhesive member 930*e*. This also imparts breathability to the first adhesive member 930*e*. In the example of FIG. 16E, the first adhesive member 930*e* has about 60% surface area remaining for coupling between the sensor base 908 and the second adhesive member 932.

Figure 16F:
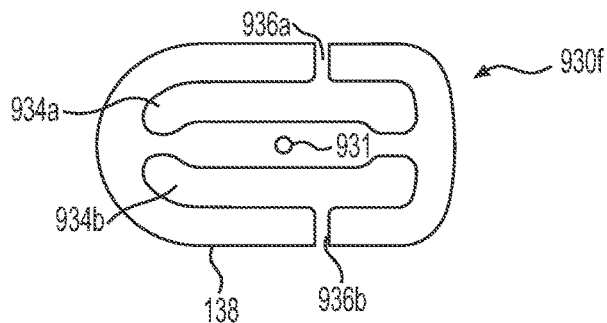

In the example of FIG. 16F, a first adhesive member 930*f* is shown. The first adhesive member 930*f* includes the first cut-out 934*a* opposite the second cut-out 934*b*, and the pair of slits 936*a*-936*b*, although in this example, the first cut-out 934*a*, the second cut-out 934*b* and the pair of slits 936*a*-936*b* have an increased surface area over that of FIG. 16D such that an additional amount of the first adhesive member 930*f* is removed. The first cut-out 934*a*, the second cut-out 934*b* and the pair of slits 936*a*-936*b* cooperate to direct moisture, fluids, etc. from near the center of the physiological characteristic sensor assembly 902 (FIG. 15) toward the perimeter 938 of the first adhesive member 930*f* This also imparts breathability to the first adhesive member 930*f* In the example of FIG. 16F, the first adhesive member 930*f* has about 50% surface area remaining for coupling between the sensor base 908 and the second adhesive member 932.

Thus, the first adhesive member 930*b*-930*f* is defined with the first cut-out 934*a*, the second cut-out 934*b* and the pair of slits 936*a*-936*b* to direct moisture, fluids, etc. from near the center of the physiological characteristic sensor assembly 902 (FIG. 15) toward the perimeter 938 of the respective first adhesive member 930*b*-930*f* The first cut-out 934*a*, the second cut-out 934*b* and the pair of slits 936*a*-936*b* also improves a breathability of the physiological characteristic sensor assembly 902 while also improving user comfort.

With reference back to FIG. 15, the second adhesive member 932 couples the physiological characteristic sensor assembly 902 to the user. In one example, the second adhesive member 932 includes a backing layer 940, a skin adhesive layer 942 and defines a central bore 944. The backing layer 940 and the skin adhesive layer 942 cooperate to define an adhesive skin patch for coupling the physiological characteristic sensor assembly 902 to the user, and for ease of illustration are shown with a nominal thickness. The backing layer 940 is composed of a nonwoven polyurethane, for example. The backing layer 940 has a first surface coupled to a respective one of the first adhesive member 930-930*f*, and an opposite second surface coupled to the skin adhesive layer 942. The skin adhesive layer 942 is composed of an acrylic adhesive, which may be painted, coated or otherwise formed on the backing layer 940. One side of the skin adhesive layer 942 is coupled to the backing layer 940, and a second opposite side is configured to be coupled to an anatomy, such as a skin of a user, when the physiological characteristic sensor assembly 902 is deployed on the user. The central bore 944 is coaxially aligned with the central bore 931 of the respective first adhesive member 930-930*f* to enable the glucose sensor 906 to pass through the second adhesive member 932. Thus, the central bore 944 is defined through both the backing layer 940 and the skin adhesive layer 942.

In one example, with reference to FIG. 15, with the physiological characteristic sensor assembly 102 assembled, the skin adhesive layer 942 is coupled to the backing layer 940 to form the second adhesive member 932. A respective first adhesive member 930-930*f*, such as one of the first adhesive members 930*b*-930*f*, is coupled to the second adhesive member 932, and is coupled to the sensor base 908. With the medical device 900 assembled, the medical device 900 may be coupled to a sensor inserter (not shown), packaged, sterilized and shipped to an end user.

Once received, the user may remove the packaging to expose the medical device 900. The user may manipulate the sensor inserter to deploy the physiological characteristic sensor assembly 902 onto the user such that the glucose sensor 906 is positioned within a tissue of the user and the skin adhesive layer 962 is coupled to the anatomy or skin of the user. With the medical device 900 coupled to the user, the user may perform their daily activities with increased comfort and breathability. In this regard, as discussed, the first cut-out 934*a*, the second cut-out 934*b* and the pair of slits 936*a*-936*b* of the first adhesive member 930*b*-93*f* cooperate to direct moisture, fluids, etc. away from the glucose sensor 906 toward the perimeter 938 of the respective first adhesive member 930*b*-930*f*, which improves breathability of the medical device 900. Moreover, the reduced bonding area of the first adhesive members 930*b*-930*f* between the physiological characteristic sensor assembly 902 and the second adhesive member 932 provides increased conformity of the medical device 900 to the anatomy of the user.

Thus, the first adhesive member 130, 130', the coupling system 204, 304, 404, 504, 604, 704, 804, 904 each cooperate with the respective medical device 100, 900 to improve the moisture vapor transmission rate and to direct moisture, fluids, etc. away from the respective medical device 100, 900. Generally, each of the first adhesive member 130, 130', the coupling system 204, 304, 404, 504, 604, 704, 804, 904 has a surface area less than 100%, which provides cut-outs or areas devoid of material to provide breathability. For example, the surface area of the first adhesive member 130 and the first adhesive member 130' is about 50%. The increased breathability provided by the first adhesive member 130, 130', the coupling system 204, 304, 404, 504, 604, 704, 804, 904 may also result in an extended wear period for the respective coupling system 104, 204, 304, 404, 504, 604, 704, 804, 904 such that user may wear the respective medical device 100, 900 for 7-10 days or more. In addition, the reduction in surface area to below 100% also enables the medical device 100, 900 to conform better to the user's anatomy, which increases comfort. In addition, the reduction in the surface area associated with the respective coupling system 104, 204, 304, 404, 504, 604, 704, 804, 904 provides a generally symmetrical design, which equally distributes forces applied to the respective coupling system 104, 204, 304, 404, 504, 604, 704, 804, 904.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A medical device, comprising:
a sensor configured to observe a characteristic of an anatomy;
a sensor base coupled to the sensor; and
a coupling system configured to couple the sensor base to the anatomy, the coupling system including a first adhesive member and a second adhesive member, the first adhesive member coupled to the sensor base, and the second adhesive member configured to couple to the anatomy, the first adhesive member including a plurality of first cut-outs, and the second adhesive member includes a backing layer, a skin adhesive layer and a plurality of second cut-outs defined through the backing layer and the skin adhesive layer from a skin-facing side of the skin adhesive layer to a sensor-base-facing side of the backing layer to enable fluid communication between the anatomy and the sensor-base-facing side of the backing layer, the backing layer coupled to the first adhesive member, the skin adhesive layer configured to directly contact and couple to the anatomy, each second cut-out of the plurality of second cut-outs includes a first portion that extends along a first axis and a second portion that extends along a second axis, the second axis perpendicular to the first axis, the first portion in communication with the second portion, a length of the first portion along the first axis is greater than a width of one of the plurality of first cut-outs, the second portion extends beyond a perimeter of the sensor base and the first portion is in communication with a respective first cut-out of the plurality of first cut-outs to direct moisture to an ambient environment surrounding the medical device.

2. The medical device of claim 1, wherein the second adhesive member defines a central bore to receive the sensor, the plurality of second cut-outs are spaced apart about the central bore and the first portion of each of the plurality of second cut-outs is defined within the perimeter of the sensor base.

3. The medical device of claim 1, wherein the plurality of first cut-outs of the first adhesive member includes a plurality of channel cut-outs, and the second portion of each of the plurality of second cut-outs of the second adhesive member is collinear with a respective one of the plurality of channel cut-outs.

4. A medical device, comprising:
a base; and
a coupling system configured to couple the base to the anatomy, the coupling system including a first adhesive member and a second adhesive member, the first adhesive member coupled to the base and the second adhesive member configured to couple to the anatomy, the first adhesive member including a plurality of first cut-outs that define a main channel and a plurality of intermediate channels, the second adhesive member including a backing layer coupled to the first adhesive member, a skin adhesive layer configured to directly contact and couple to the anatomy and a plurality of second cut-outs defined through the backing layer and the skin adhesive layer from a skin-facing side of the skin adhesive layer to a sensor-base-facing side of the backing layer to enable fluid communication between the anatomy and the sensor-base-facing side of the backing layer, each second cut-out of the plurality of second cut-outs includes a first portion that extends along a first axis and a second portion that extends along a second axis, the second axis perpendicular to the first axis, the first portion in communication with the second portion and the main channel, a length of the first portion along the first axis is greater than a width of one of the plurality of first cut-outs, and the second portion is in communication with the respective intermediate channel of the plurality of intermediate channels, wherein the first portion of each of the plurality of second cut-outs is defined within a perimeter of the base and the second portion of each of the plurality of second cut-outs extends beyond the perimeter of the base to direct moisture to an ambient environment surrounding the medical device.

5. The medical device of claim 4, wherein the second adhesive member defines a central bore, and the plurality of second cut-outs are spaced apart about the central bore.

6. The medical device of claim 1, wherein the first adhesive member includes a plurality of first cut-outs that define a main channel and a plurality of intermediate channels, the first portion is in communication with the second portion and the main channel, the second portion extends beyond and across a respective intermediate channel of the plurality of intermediate channels, and the second portion is in communication with the respective intermediate channel of the plurality of intermediate channels.

7. The medical device of claim 1, wherein the first portion of each second cut-out is located within the perimeter of the sensor base.

8. The medical device of claim 4, wherein the first adhesive member includes a central hub section and wherein the main channel has an annular shape that extends around the central hub section.

9. The medical device of claim 7, wherein the second portion of each second cut-out is located partially within the perimeter of the sensor base and has an end located beyond the perimeter of the sensor base.

10. The medical device of claim 1, wherein the first portion of each second cut-out has a longitudinal dimension extending along the first axis, and wherein the second portion of each second cut-out has a longitudinal dimension that extends from a central location of the longitudinal dimension of the of the first portion of the second cut-out to an end located beyond the perimeter of the sensor base.

11. The medical device of claim 1, wherein a width of the second portion is less than the width of the one of the plurality of first cut-outs.

* * * * *